(12) United States Patent
Yamaya

(10) Patent No.: US 11,857,162 B2
(45) Date of Patent: Jan. 2, 2024

(54) ENDOSCOPE

(71) Applicant: OLYMPUS CORPORATION, Tokyo (JP)

(72) Inventor: Koji Yamaya, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 651 days.

(21) Appl. No.: 16/988,900

(22) Filed: Aug. 10, 2020

(65) Prior Publication Data

US 2020/0367732 A1 Nov. 26, 2020

Related U.S. Application Data

(63) Continuation of application No. PCT/JP2018/045080, filed on Dec. 7, 2018.

(30) Foreign Application Priority Data

Feb. 15, 2018 (JP) .................................. 2018-024914

(51) Int. Cl.
*A61B 1/018* (2006.01)
*A61B 1/00* (2006.01)
(Continued)

(52) U.S. Cl.
CPC ............ *A61B 1/018* (2013.01); *A61B 1/0051* (2013.01); *A61B 1/0057* (2013.01);
(Continued)

(58) Field of Classification Search
CPC .......................... A61B 1/00098; A61B 1/0057
See application file for complete search history.

(56) References Cited

U.S. PATENT DOCUMENTS 4,198,959 A * 4/1980 Otani ................. A61B 1/00137
600/153
4,452,236 A * 6/1984 Utsugi .............. A61M 25/0147
600/107

(Continued)

FOREIGN PATENT DOCUMENTS

EP  3 272 268 A1  1/2018
JP  6-315457 A  11/1994
(Continued)

OTHER PUBLICATIONS

International Search Report dated Mar. 12, 2019 received in PCT/JP2018/045080.

*Primary Examiner* — Matthew J Kasztejna
(74) *Attorney, Agent, or Firm* — Scully, Scott, Murphy & Presser, P.C.

(57) ABSTRACT

An endoscope includes: a distal-end constituting portion provided at a distal end portion of an insertion portion; a distal end cover attachable to and detachable from the distal-end constituting portion; a movable portion provided in the distal-end constituting portion; a connecting member provided at the movable portion; a pulling and relaxing member that drives the movable portion by being pulled or relaxed; a connecting body provided to the pulling and relaxing member, and attachable to and detachable from the connecting member, the connecting body being detachable from the connecting member in a state where the distal end cover is removed from the distal-end constituting portion; and a tube having flexibility through which the pulling and relaxing member is inserted, the tube including a distal end and a proximal end and being disposed in the distal end portion, the proximal end being detachably connected to the distal-end constituting portion.

20 Claims, 18 Drawing Sheets

(51) Int. Cl.
    *A61B 1/005*     (2006.01)
    *A61B 1/05*     (2006.01)
    *A61B 1/06*     (2006.01)

(52) U.S. Cl.
    CPC ...... *A61B 1/00087* (2013.01); *A61B 1/00091* (2013.01); *A61B 1/00094* (2013.01); *A61B 1/00098* (2013.01); *A61B 1/00101* (2013.01); *A61B 1/05* (2013.01); *A61B 1/0676* (2013.01)

(56) References Cited

U.S. PATENT DOCUMENTS

| | | | |
|---|---|---|---|
| 5,707,344 | A | 1/1998 | Nakazawa et al. |
| 6,582,357 | B2 * | 6/2003 | Ouchi ................ A61B 1/00177 600/134 |
| 2007/0208221 | A1 * | 9/2007 | Kennedy, II ........... A61B 1/018 604/165.01 |
| 2018/0035869 | A1 | 2/2018 | Yamaya |
| 2018/0289245 | A1 | 10/2018 | Yamaya |

FOREIGN PATENT DOCUMENTS

| | | | |
|---|---|---|---|
| JP | 6-315458 | A | 11/1994 |
| JP | 8-196505 | A | 8/1996 |
| JP | 8-243076 | A | 9/1996 |
| JP | 9-299315 | A | 11/1997 |
| JP | 2004-141315 | A | 5/2004 |
| WO | 2017/002587 | A1 | 1/2017 |
| WO | 2017/122559 | A1 | 7/2017 |

\* cited by examiner

ENDOSCOPE

CROSS-REFERENCE TO RELATED APPLICATIONS

This application is a continuation application of PCT/JP2018/045080 filed on Dec. 7, 2018 and claims benefit of Japanese Application No. 2018-024914 filed in Japan on Feb. 15, 2018, the entire contents of which are incorporated herein by this reference.

BACKGROUND OF THE INVENTION

1. Field of the Invention

The present invention relates to an endoscope configured to drive a movable member disposed in a distal end portion of an insertion portion of the endoscope with an operation wire.

2. Description of the Related Art

Conventionally, endoscopes have been widely used in medical fields. Such endoscopes are configured to be capable of observing organs in a body cavity and the like by inserting an elongated insertion portion into a body cavity. In a case of causing observation images of organs in a body cavity to be displayed on a monitor, an endoscope, which includes a solid-state image pickup device such as a charge coupled device (CCD) disposed in an image pickup section provided at the distal end or the rear end of the insertion portion of the endoscope, is used, for example.

Signals outputted from an image pickup device provided in an endoscope are converted into video signals by an image processing apparatus as an external device of the endoscope and provided separately from an external camera, etc., and the video signals are outputted to the monitor. The endoscope and the image processing apparatus, which are configured separately from each other, are connected to each other through a connector for endoscope.

Some of such endoscopes include, at a distal end portion thereof, a raising base (forceps elevator), as a movable member, which raises and lowers a treatment instrument such as a forceps. For example, Japanese Patent Application Laid-Open Publication No. 6-315457 discloses a forceps elevator apparatus for endoscope which prevents a contaminated liquid to enter from the tip side of the distal end portion of the endoscope into a gap between the forceps elevating operation wire and the operation wire guiding tube during the use of the endoscope, and which enables the gap to be easily cleaned after the use of the endoscope.

SUMMARY OF THE INVENTION

An endoscope according to one aspect of the present invention includes: a distal-end constituting member provided at a distal end portion of an insertion portion; a distal end cover configured to be attachable to and detachable from the distal-end constituting member; a movable member provided in the distal-end constituting member; a connecting member provided at the movable member; a pulling and relaxing member configured to drive the movable member by being pulled or relaxed; a connecting body provided to the pulling and relaxing member, the connecting body being configured to be attachable to and detachable from the connecting member, the connecting body being detachable from the connecting member in a state where the distal end cover is removed from the distal-end constituting member; and a tube having flexibility through which the pulling and relaxing member is inserted, the tube being disposed in the distal end portion and including a distal end and a proximal end detachably connected to the distal-end constituting member.

DETAILED DESCRIPTION OF THE PREFERRED EMBODIMENT(S)

Hereinafter, description will be made by taking one aspect of an endoscope as an example. Note that each of the drawings based on each embodiment is a pattern diagram, and care should be taken to the fact that the relationship between the thicknesses and widths of the respective members, a ratio of the thickness of a certain member to that of another member, and the like are different from the actual ones, and there is a case where the respective drawings include parts in which the relationships and ratios among the dimensions are different.

In addition, the endoscope in the configuration description below will be described by taking, what is called, a flexible endoscope as an example. Such a flexible endoscope has a flexible insertion portion for allowing insertion into an upper digestive tract, a lower digestive tract, and the like in a living body. However, the present invention is not limited to such an endoscope. The present invention provides a technique applicable to, what is called, a rigid endoscope having a rigid insertion portion to be used for surgery.

First Embodiment

Hereinafter, an endoscope according to one aspect of the present invention will be described with reference to drawings.

Figure 1:
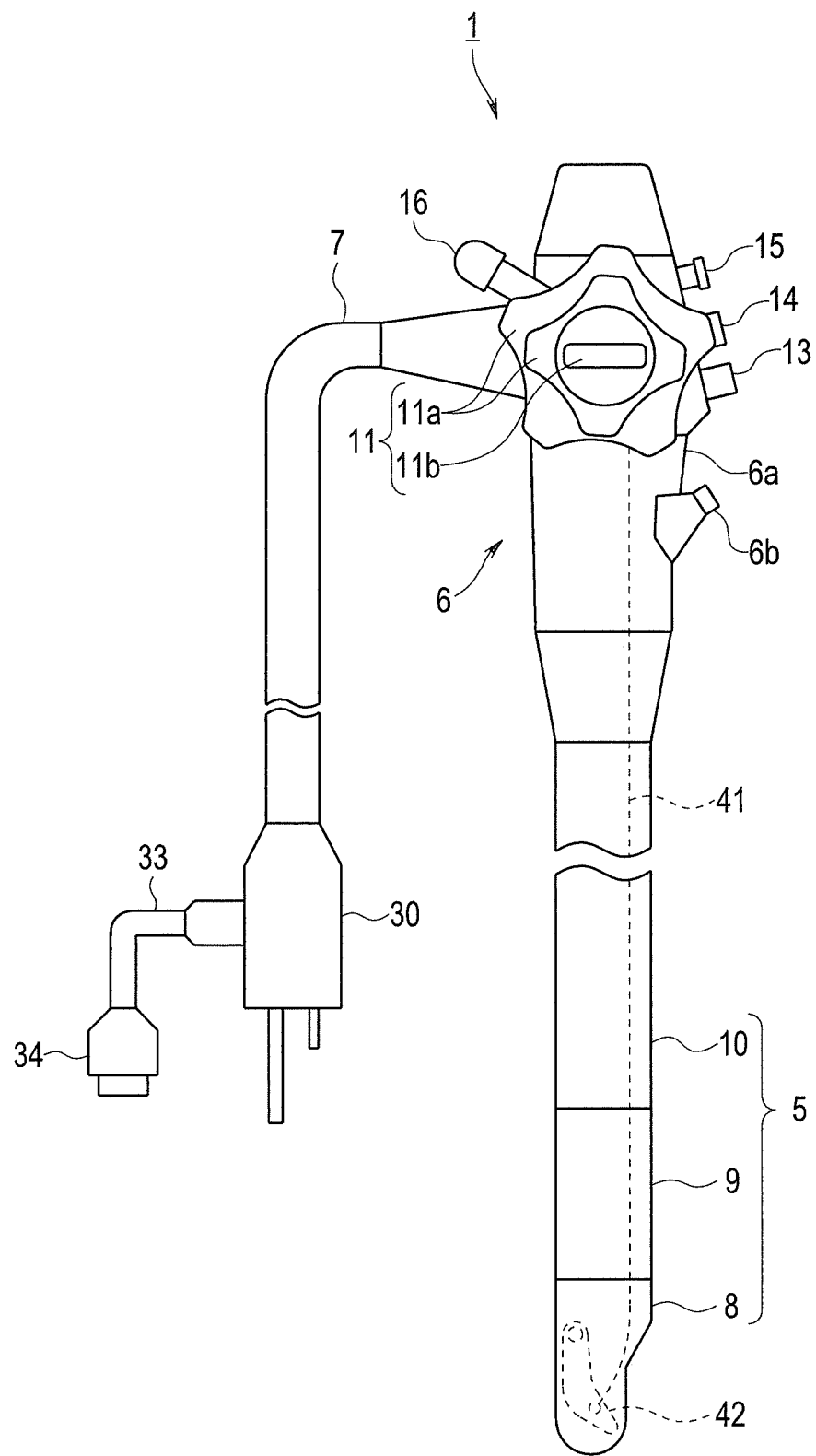
FIG. 1 is a side view illustrating a configuration of an endoscope according to the present invention.
Figure 2:
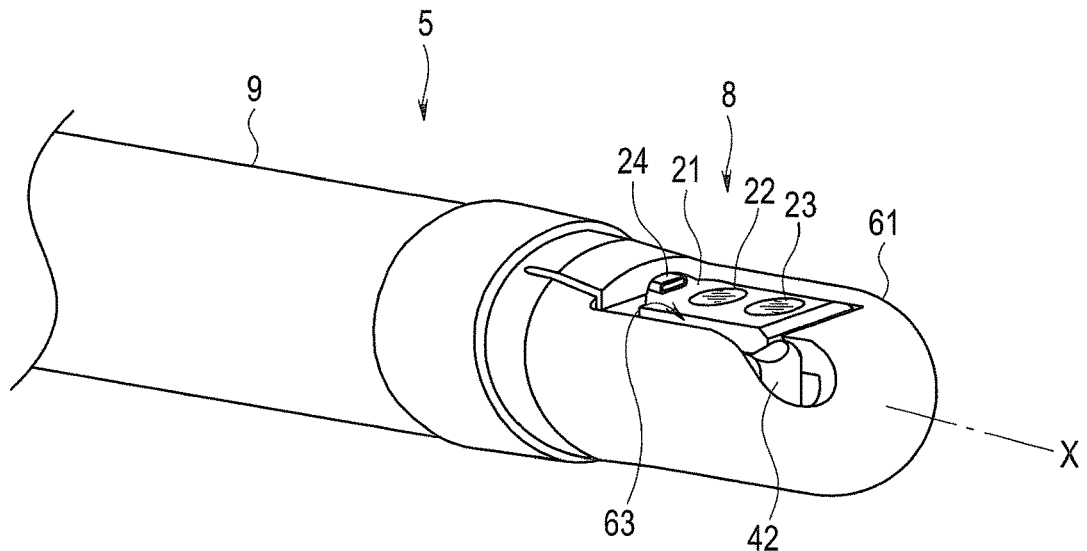
FIG. 2 is a perspective view illustrating a configuration of a distal end portion of an insertion portion of the endoscope according to the present invention.
Figure 3:
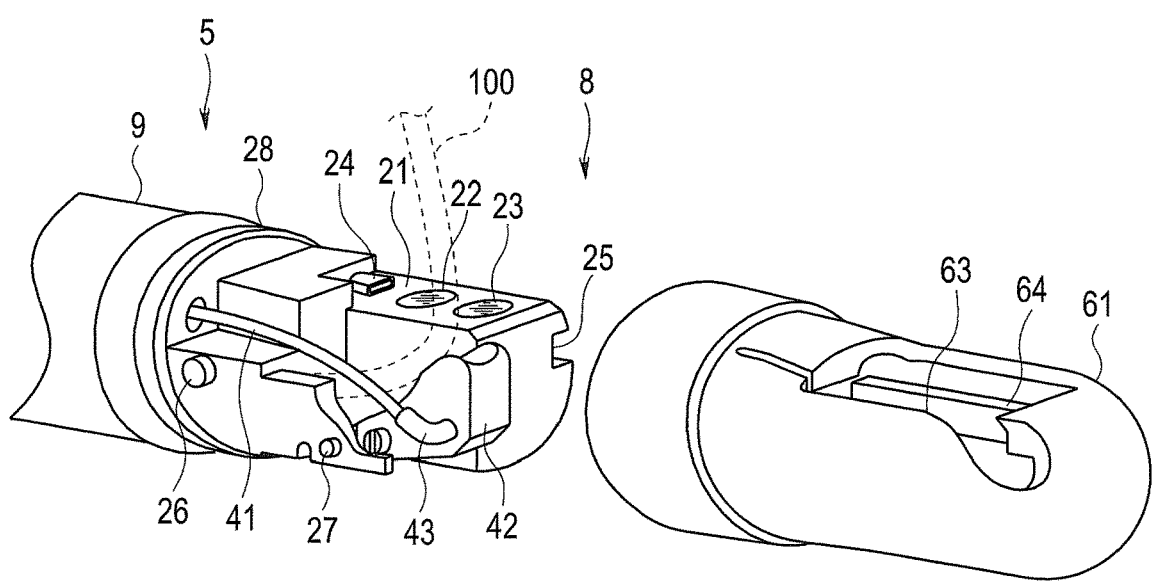
FIG. 3 is a perspective view illustrating a configuration of the distal end portion from which a distal end cover is removed.
Figure 4:
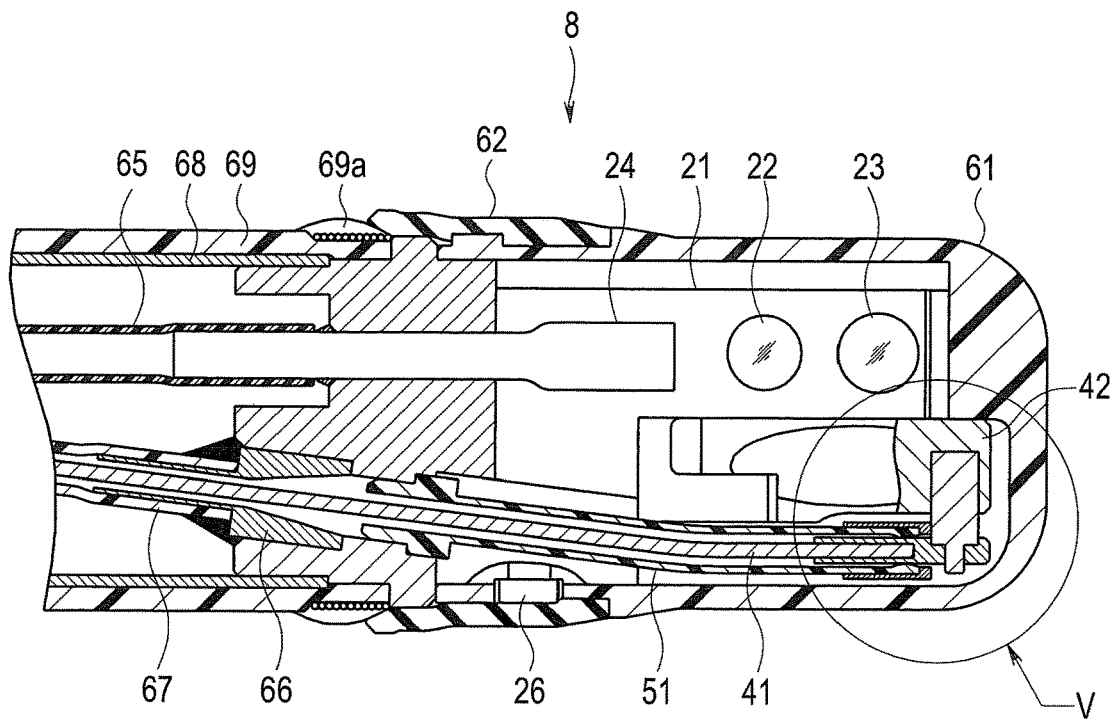
FIG. 4 is a cross-sectional view of the distal end portion as viewed from above.
Figure 5:
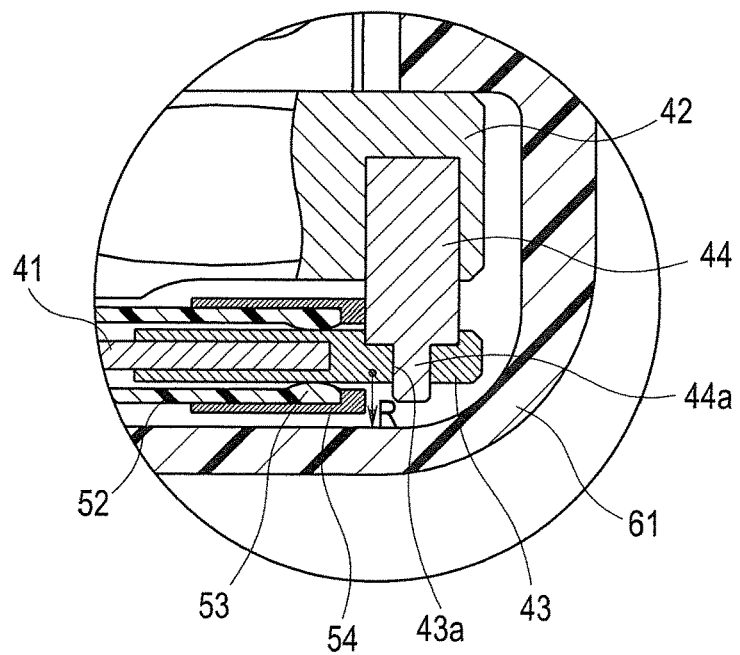
FIG. 5 is an enlarged cross-sectional view of the part indicated by the circle V in FIG. 4.
Figure 6:
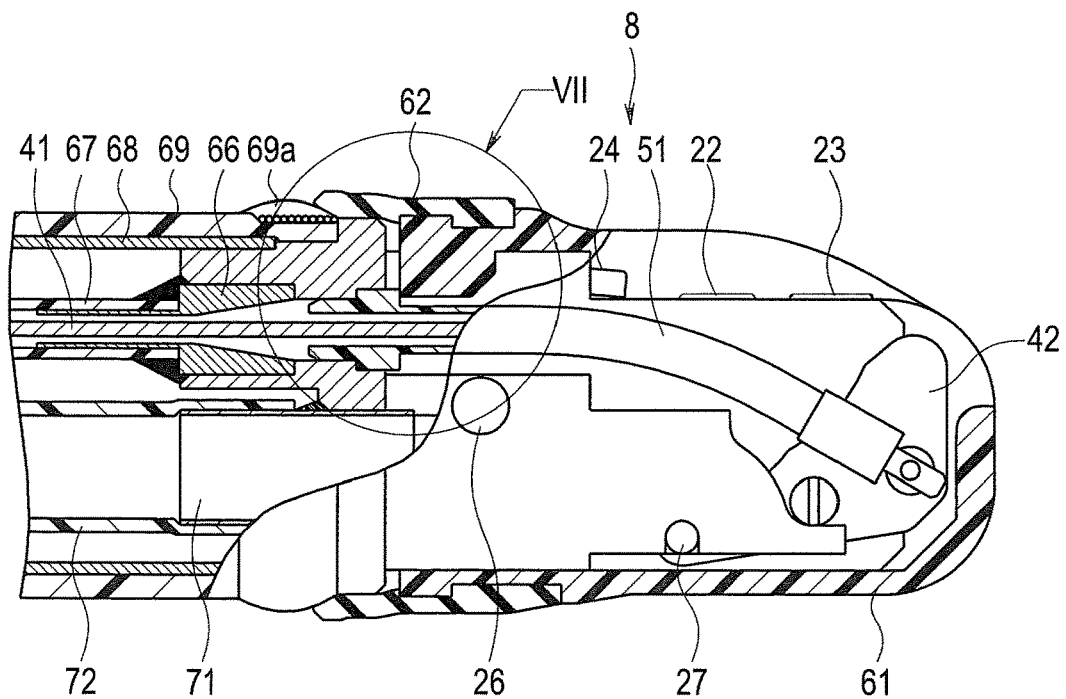
FIG. 6 is a cross-sectional view of the distal end portion as viewed from a lateral side.
Figure 7:
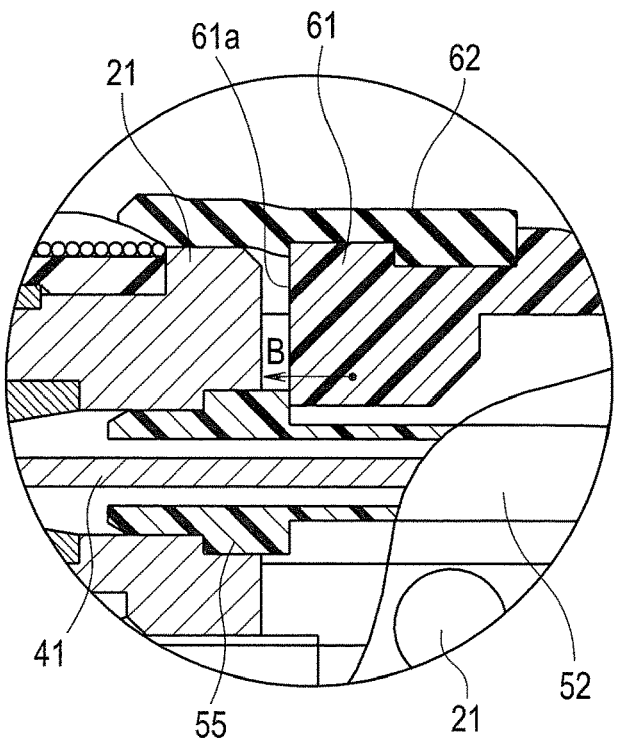
FIG. 7 is an enlarged cross-sectional view of the part indicated by the circle VII in FIG. 6.
Figure 8:
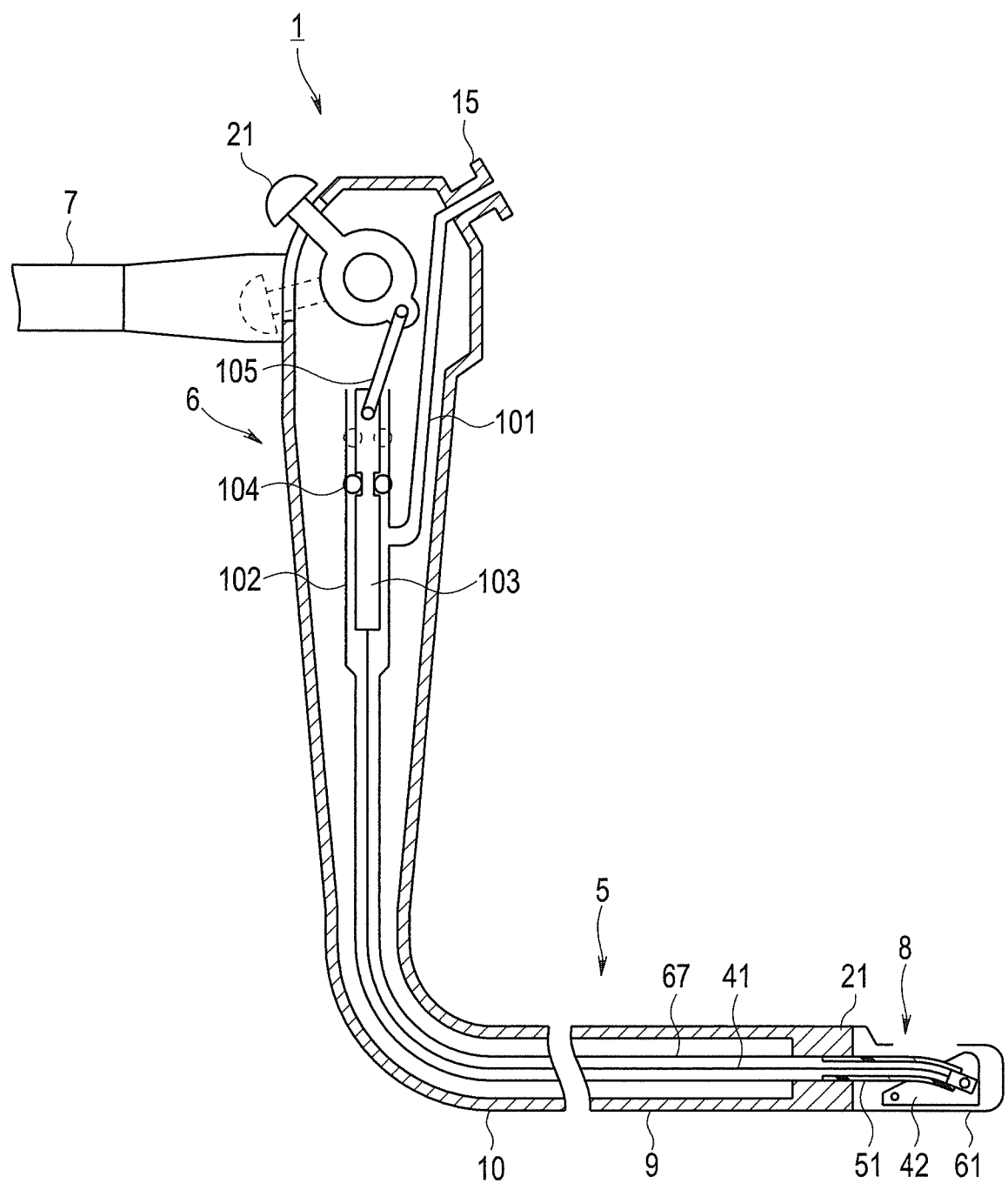
FIG. 8 is a cross-sectional view schematically illustrating an inside of the endoscope.
Figure 9:
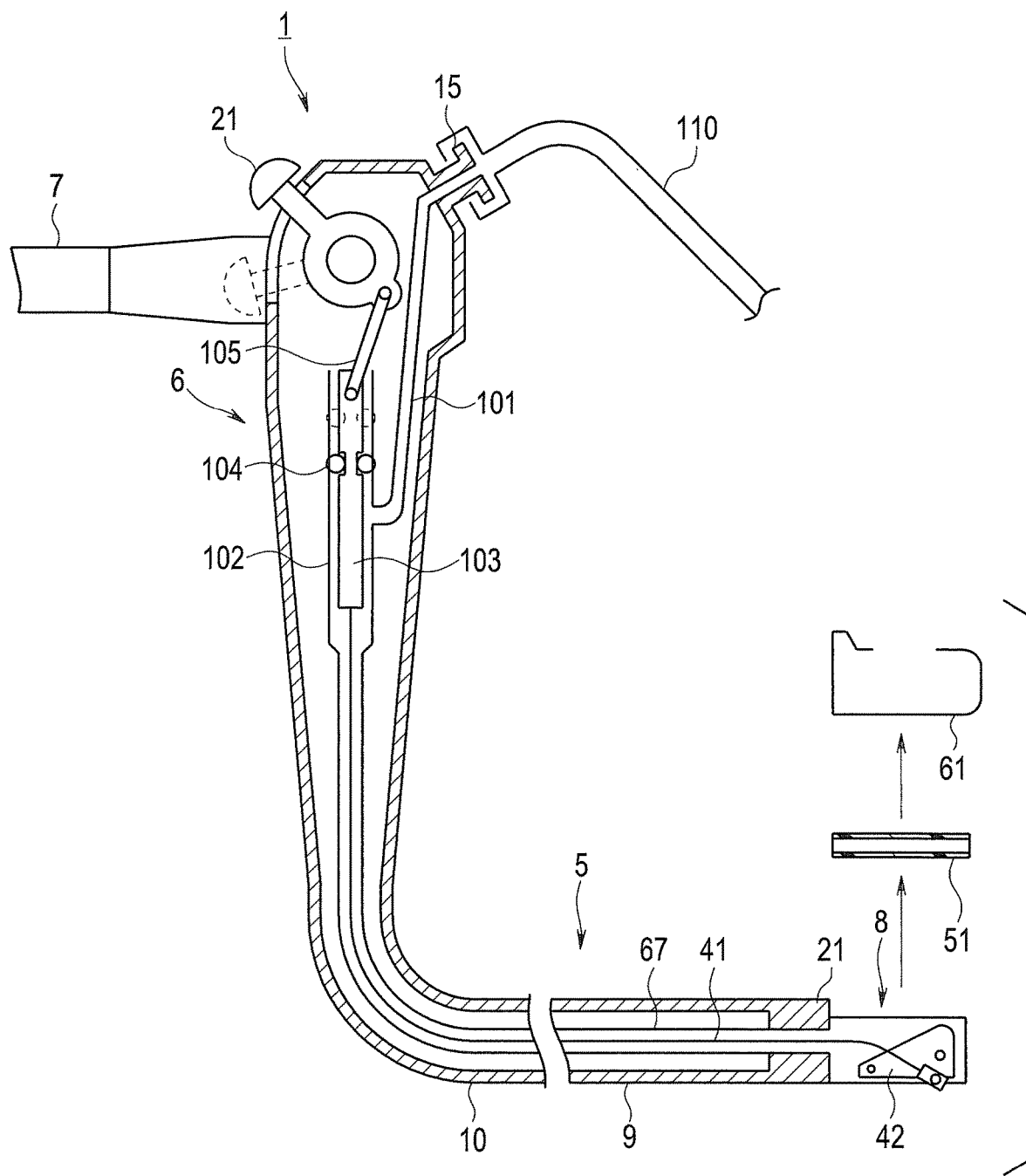
FIG. 9 is a cross-sectional view schematically illustrating the inside of the endoscope from which the distal end cover and a flexible tube are removed and to which a cleaning tube is connected.
Figure 10:
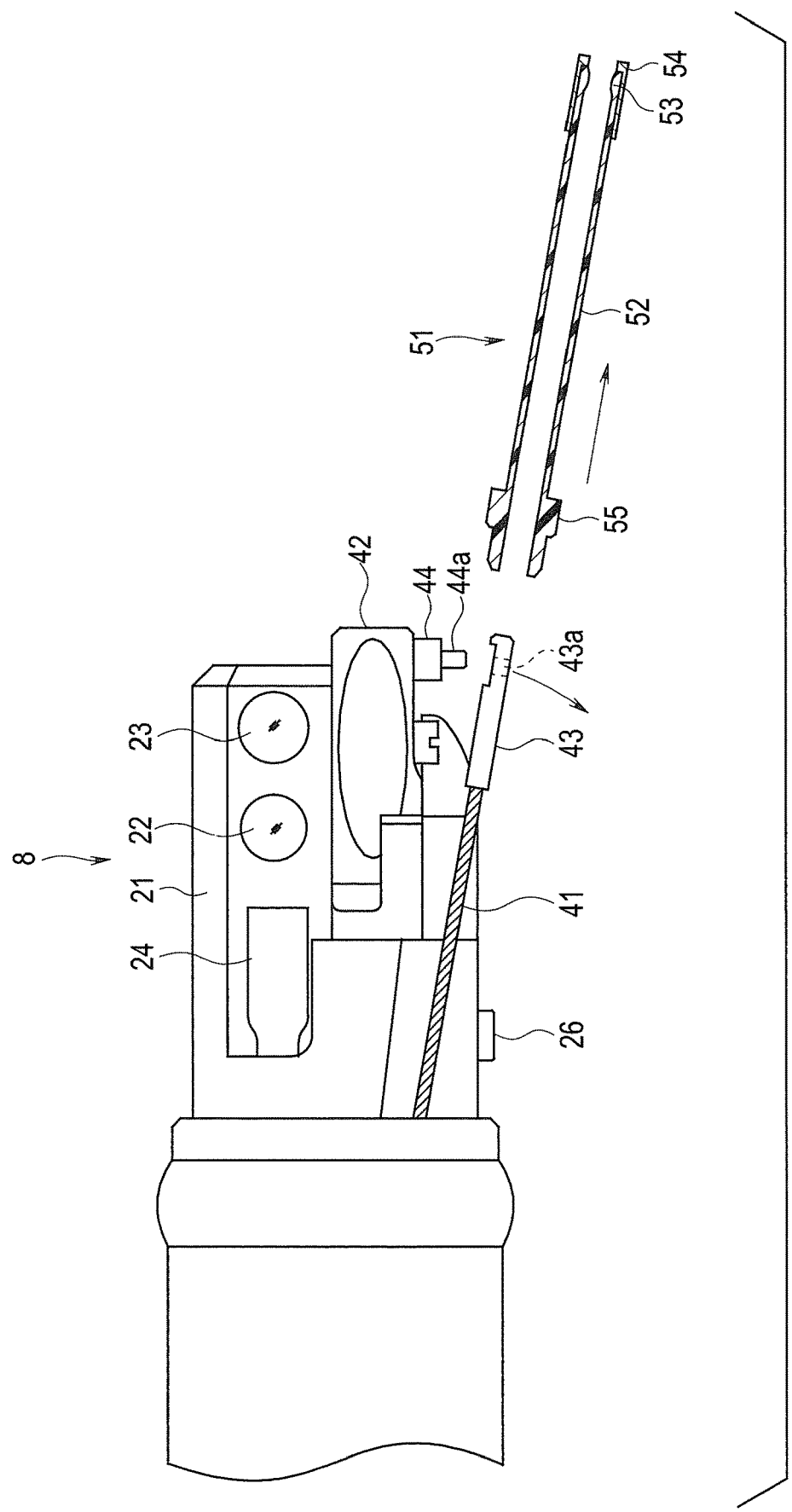
FIG. 10 is a top view illustrating the distal end portion from which the distal end cover is removed and the flexible tube is detached.

Note that FIG. 1 is a side view illustrating a configuration of the endoscope, FIG. 2 is a perspective view illustrating a configuration of a distal end portion of an insertion portion of the endoscope, FIG. 3 is a perspective view illustrating the configuration of the distal end portion from which a distal end cover is removed, FIG. 4 is a cross-sectional view of the distal end portion as viewed from above, FIG. 5 is an enlarged cross-sectional view of the part indicated by the circle V in FIG. 4, FIG. 6 is a cross-sectional view of the distal end portion as viewed from a lateral side, FIG. 7 is an enlarged cross-sectional view of the part indicated by the circle VII in FIG. 6, FIG. 8 is a cross-sectional view schematically illustrating an inside of the endoscope, FIG. 9 is a cross-sectional view schematically illustrating the inside of the endoscope from which the distal end cover and a flexible tube are removed and to which a cleaning tube is connected, and FIG. 10 is a top view illustrating the distal end portion from which the distal end cover is removed and the flexible tube is detached.

An endoscope 2 according to the present embodiment includes an insertion portion 5, an operation portion 6, and a universal cable 7, as illustrated in FIG. 1. The insertion portion 5 is an elongated member configured to be inserted into an observation target from the distal end side in the longitudinal axis direction. The insertion portion 5 includes, in a linked manner, a distal end portion 8, a bending portion 9, and a flexible tube portion 10.

The distal end portion 8 incorporates an illumination optical system including a light guide and an image pickup optical system including an image pickup apparatus, and includes, on the distal end surface thereof, a nozzle, and a suction port which serves both as and a treatment instrument lead-out port (none of these are illustrated here).

The distal end portion 8 includes an observation window and an illumination window that are formed so as to have a predetermined angle with respect to an insertion direction of the insertion portion 5. The distal end portion 8 also includes a raising base (forceps elevator) 42 which is a movable portion. The raising base is a direction changing portion configured to raise the treatment instrument to change a direction of the treatment instrument in an observation direction.

The raising base 42 is connected to a raising base operation wire (hereinafter, shortly referred to as a wire) 41 which is a pulling and relaxing member. The wire 41 is a long member inserted into the insertion portion 5 and the operation portion 6. The wire 41 is pulled and relaxed, to thereby cause the raising base 42 to be raised and lowered. Note that the wire 41 is pulled and relaxed by operating a raising base operation lever 16.

The bending portion 9 is configured to be bendable in four directions, i.e., up, down, left, and right directions, for example. The flexible tube portion 10 is a long and flexible tubular member.

The operation portion 6 includes a grasping portion 6a. The grasping portion 6a is connected to the proximal end portion of the insertion portion 5, and a treatment instrument insertion port 6b is disposed on the grasping portion 6a.

The operation portion 6 is provided with a bending operation portion 11, an air/water feeding button 13, a suction button 14, a cleaning tube connector 15, and the like. In addition, the operation portion 6 is provided with the raising base operation lever 16 as an operation member.

The bending operation portion 11 includes a bending operation knob 11a for performing bending operation of the bending portion 9 of the insertion portion 5 and a lock lever 11b for locking the bending operation knob 11a at a desired rotation position.

The universal cable 7 is extended from a side surface of the operation portion 6. The universal cord 7 includes, at an end portion thereof, an endoscope connector 30 configured to be connected to a light source apparatus as an external device. A signal transmission cable 33 is extended from a side portion of the endoscope connector 30. At the extending end side of the signal transmission cable 33, an electrical connector 34 configured to be connected to a video processor is provided.

As illustrated in FIGS. 2 and 3, at the distal end portion 8 of the insertion portion 5, a distal-end constituting portion 21 made of metal such as stainless steel is provided. In the distal-end constituting portion 21, the raising base 42, which is made of metal such as stainless steel, is pivotally disposed.

The distal-end constituting portion 21 includes, on one side surface thereof, an observation window 22 and an illumination window 23. The one side surface is orthogonal to an insertion axis X illustrated in FIG. 2. In addition, the distal-end constituting portion 21 includes a nozzle 24 for feeding air and water toward the observation window 22 and the illumination window 23.

The raising base 42 is disposed so as to be pivotable, and is pivotally supported to the distal-end constituting portion 21 by a pivot shaft 27. The wire 41 is detachably connected to the raising base 42 in the distal end portion 8. The wire 41 is inserted through a flexible tube 51 which is made of silicone rubber or the like and which is pliable and stretchable. The wire 41 is pulled and relaxed, to thereby cause the raising stand 42 to be raised and lowered around the pivot shaft 27.

A distal end cover 61 made of synthetic resin such as plastic is detachably mounted on the distal end constituting portion 21. The distal end cover 61 includes a rubber ring 62 disposed in the circumferential direction on the proximal end side of the distal end cover. In addition, the distal end cover 61 includes an opening portion 63 that allows exposure of the observation window 22 and the illumination window 23 and allows a treatment instrument 100, which is raised and lowered by the raising base 42, to be led out.

The distal end cover 61 is mounted so as to cover the distal-end constituting portion 21. When the distal end cover 61 is mounted on the distal-end constituting portion 21, a regulating projection portion 64 provided on the inner circumferential surface of the distal end cover 61 is engaged in a regulating recessed portion 25 formed on the distal-end constituting portion 21. Such a configuration defines the mounting direction of the distal end cover 61 to the distal-end constituting portion 21.

Then, the distal end cover 61 is mounted to be fixed to the distal-end constituting portion 21 by a locking recessed portion 29 formed on the inner circumferential portion of the distal end cover 61 is engaged with a locking pin 26 provided so as to protrude from the side portion of the distal-end constituting portion 21.

As illustrated in FIG. 4, the distal end portion 8 is configured such that a rigid tubular member 68 is fitted to the proximal end part of the distal-end constituting portion 21. The tubular member 68 is provided at the distal-most of the bending pieces, not illustrated, provided in the bending portion 9.

On the outer circumference of the tubular member 68, a tubular bending rubber 69 is provided. The bending rubber 69 integrally covers the proximal end outer circumferential portion of the distal-end constituting portion 21. The distal end part of the bending rubber 69 is fixed and adhered by a thread-wound adhering portion 69a.

The nozzle 24 has a middle part inserted through the distal-end constituting portion 21, and has the proximal end part to which an air/liquid feeding tube 65 is connected. In addition, a wire covering tube 67, which is a coil tube, for example, and which covers the wire 41 disposed in the insertion portion 5, is connected to a pipe sleeve 66 fitted to the distal-end constituting portion 21. Note that the wire 41 is inserted from the distal-end constituting portion 21 into the flexible tube 51 to be connected to the raising base 42.

A wire terminal member 43 having a substantially columnar outer shape is provided at the distal end of the wire 41, as illustrated in FIG. 5. The wire terminal member 43 is a connecting body configured to be attachable to and detachable from the raising base 42. The wire terminal member 43 has a through hole 43a pierced in the direction orthogonal to the longitudinal axis of the wire 41 to be connected to the raising base 42.

The flexible tube 51 covering the wire 41 in the distal end portion 8 includes a projection portion 53 formed in a circumferential direction on the distal end inner circumferential portion of the tube main body 52 of the flexible tube 51. In addition, a distal end pipe sleeve member 54 made of metal such as stainless steel is provided on the distal end outer circumferential portion of the tube main body 52.

Note that the projection portion 53 of the tube main body 52 is brought into close contact with the outer circumferential surface of the wire terminal member 43 provided at the distal end of the wire 41, to retain water-tightness. In addition, the distal end pipe sleeve member 54 prevents the deformation of the distal end part of the tube main body 52 due to bulging of the distal end part in the outer diameter direction.

A wire attaching member 44, which is a wire connecting portion, is fitted to the raising base 42 such that the wire attaching member 44 protrudes from the side portion in the transverse direction of the raising base 42. The transverse direction is orthogonal to the longitudinal direction of the wire 41. The wire attaching member 44 includes, at the end portion thereof, a protrusion 44a having a small diameter.

The protrusion 44a is inserted into and extracted from the through hole 43a of the wire terminal member 43, to thereby cause the wire terminal member 43 to be attached to and detached from the raising base 42. Such a configuration enables the wire 41 to be attached to and detached from the raising base 42.

Note that the connecting part between the wire 41 and the raising base 42 is configured such that, when the distal end cover 61 is mounted on the distal-end constituting portion 21, the movement of the wire terminal member 43 in the direction of the arrow R is regulated by the inner side surface of the distal end cover 61, to thereby prevent the wire terminal member 43 from falling off from the protrusion 44a of the wire attaching member 44.

Such a configuration prevents the wire 41 from being detached from the raising base 42, to thereby prevent the flexible tube 51 from coming off from the wire 41.

As illustrated in FIG. 6, the distal-end constituting portion 21 includes a connecting tube 71 fitted to the proximal end part thereof. A treatment instrument channel 72 which is a tubular body is connected to the connecting tube 71. Note that a treatment instrument (not illustrated) inserted through the treatment instrument channel 72 is introduced to reach the distal end portion 8, and the leading-out direction of the treatment instrument is changed by the raising base 42 being raised and lowered.

As illustrated in FIG. 7, an outward flange 55 serving as a proximal end seal portion is formed at the proximal end part of the flexible tube 51. Note that the proximal end part of the flexible tube 51 is engaged with the distal-end constituting portion 21, and when the distal end cover 61 is mounted on the distal-end constituting portion 21, a part of the proximal end surface 61a of the distal end cover 61 is brought into contact with the end surface on the distal end side of the outward flange 55. As a result, the outward flange 55 is pressed toward the proximal end side indicated by the arrow B.

This causes the outward flange 55 of the flexible tube 51 to fit in a recessed engaging portion for engaging the distal-end constituting portion 21 and the flexible tube 51, to be pressed toward the proximal end side. As a result, water-tightness of the connecting part between the flexible tube 51 and the distal-end constituting portion 21 is retained.

As illustrated in FIG. 8, an endoscope 1 includes, in the operation portion 6, a cleaning conduit 101 communicating with the cleaning tube connector 15. The cleaning conduit 101 is connected to a cylinder 102.

The cylinder 102 includes inside thereof a wire shaft 103, which is a piston, so as to be movable forward and backward. The wire shaft 103 includes an O-ring 104 for retaining water-tightness and a link member 105. The O-ring 104 is provided at the middle part of the outer circumferential portion of the wire shaft 103, and the link member 105 is pivotally connected to the proximal end of the wire shaft 103.

The link member 105 is pivotally connected to the raising base operation lever 16. The cylinder 102 communicates with the wire covering tube 67 as a wire insertion conduit.

In the endoscope 1 configured as described above, as illustrated in FIG. 9, at the time of cleaning and disinfecting, the cleaning tube 110 is connected to the cleaning tube connector 15 and liquids such as a cleaning solution, a disinfectant solution, alcohol, and the like are sent through the cleaning tube 110, to thereby perform cleaning, disinfecting and flushing processing on the inside of the wire covering tube 67.

At this time, the distal end cover 61 of the distal end portion 8 is removed from the distal-end constituting portion 21, and the flexible tube 51 is pulled out from the wire 41.

Specifically, after the distal end cover 61 is removed from the distal-end constituting portion 21, as illustrated in FIG. 10, the wire terminal member 43 provided at the distal end of the wire 41 is pulled out from the wire attaching member 44 of the raising base 42 toward the lateral side to be detached. Then, the flexible tube 51 is pulled out from the wire 41 toward the distal end side.

Thus, in the endoscope 1, the distal end cover 61 of the distal end portion 8 is removed, to thereby enable the flexible tube 51 provided in the distal end portion 8 to be easily removed from the wire 41. As a result, the distal-end constituting portion 21 is open, and also the distal end part of the wire 41 is brought into a completely exposed state.

In this state, the endoscope 1 allows the outer surface of the distal-end constituting portion 21 having a complicated shape to be subjected to cleaning, disinfecting, and flushing processing easily. In addition, liquids such as a cleaning solution, a disinfectant solution, and alcohol are sent into the wire covering tube 67, to thereby enable the inside of the wire covering tube 67 and the wire 41 to be cleaned, disinfected, and flushed easily.

Furthermore, in the endo scope 1, even in a case where the flexible tube 51 through which the wire 41 is inserted and which is provided in the distal end portion 8 is damaged by the treatment instrument raised and lowered by the raising base 42 contacting the flexible tube 51, replacement of the flexible tube 51 can be easily performed by removing the distal end cover 61 from the distal-end constituting portion 21.

Note that the distal end cover 61 and the flexible tube 51, which have been removed from the distal end portion 8, can be easily cleaned, disinfected, and flushed. The distal end cover 61 and the flexible tube 51 may be disposable so as to be disposed after each use.

As described above, the endoscope 1 is configured such that the flexible tube 51 provided in the distal end portion 8 can be easily removed, to thereby be capable of reducing the efforts at the time of performing cleaning, disinfecting and flushing processing. That is, such a configuration contributes to a time reduction in these processes and a reduction in the burden of the cleaning and disinfecting workers who are medical workers.

As described above, the endoscope 1 has a configuration which enables easy replacement, cleaning, disinfecting, flushing and the like of the flexible tube 51 covering the wire 41 that drives the raising base 42 which is a movable portion provided in the distal end portion 8 of the insertion portion 5, which leads to a reduction in the burden of the medical workers.

(First Modification)

Figure 11:
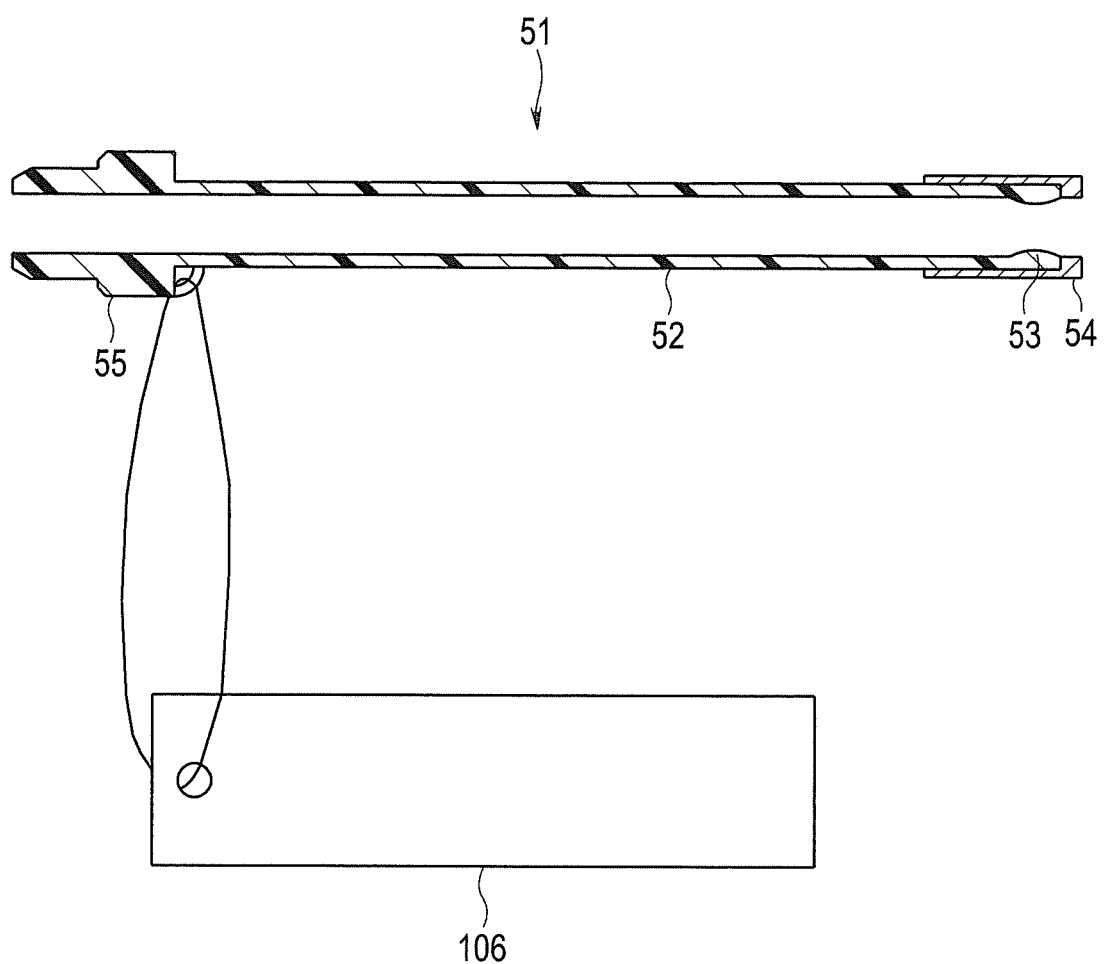
FIG. 11 is a cross-sectional view illustrating a configuration of the flexible tube to which a tag is attached, according to a first modification.

FIG. 11 is a cross-sectional view illustrating a configuration of a flexible tube to which a tag is attached, according to the first modification.

The flexible tube 51 may be attached with a tag 106 indicating that the flexible tube is unused or has been cleaned and disinfected. The tag 106 may be cut off immediately before the endoscopic examination. Attaching the tag 106 prevents a use of the contaminated flexible tube 51, forgetting to clean and disinfect the used flexible tube 51, and the like.

Note that the tag 106 preferably has a size and a length which are enough to be noticeable or a size and a length for allowing the tag to be reflected in an endoscopic image.

(Second Modification)

Figure 12:
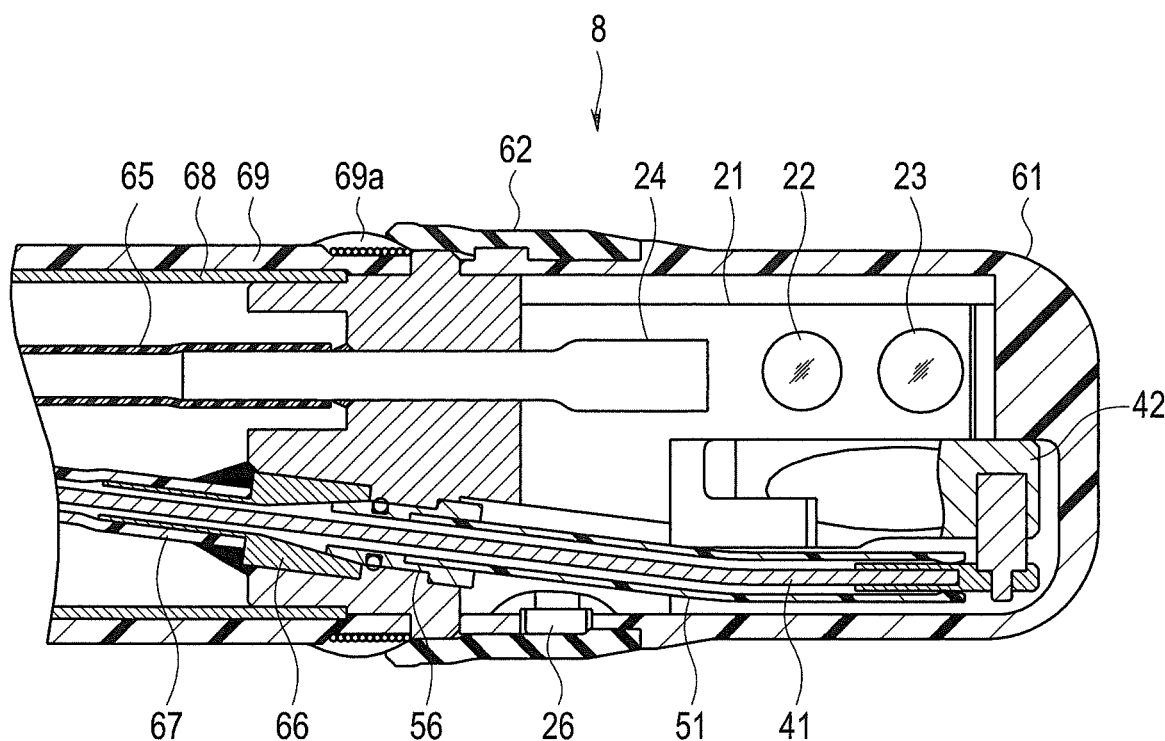
FIG. 12 is a cross-sectional view of a distal end portion of a second modification as viewed from above.
Figure 13:
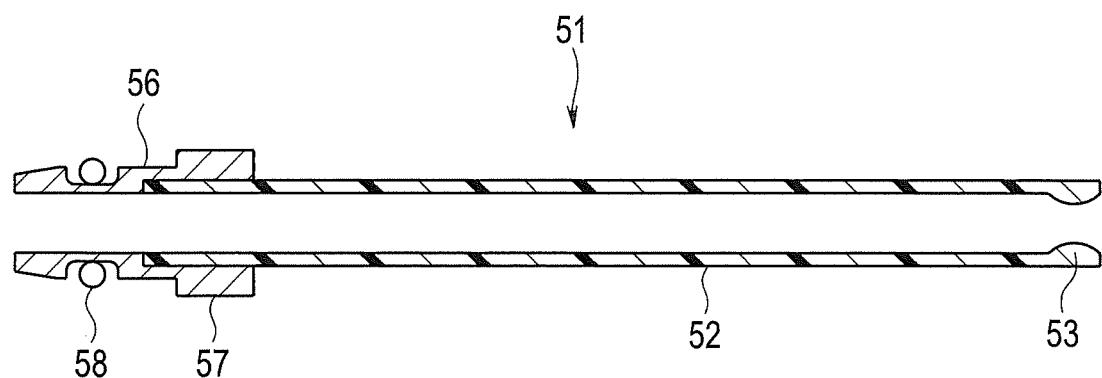
FIG. 13 is a cross-sectional view illustrating a configuration of a flexible tube according to the second modification.

FIG. 12 is a cross-sectional view of a distal end portion of the second modification as viewed from above, and FIG. 13 is a cross-sectional view illustrating a configuration of a flexible tube according to the second modification.

As illustrated in FIGS. 12 and 13, the flexible tube 51 may include, at the proximal end part thereof, a proximal end pipe sleeve 56 made of metal such as stainless steel, or made of rigid resin.

Note that, as illustrated in FIG. 13, the proximal end pipe sleeve 56 is provided with an outward flange 57 and an O-ring 58 for retaining water-tightness. The O-ring 58 is provided on the outer circumferential portion of the proximal end pipe sleeve 56 so as to be located on the proximal end side with respect to the outward flange 57.

Note that the flexible tube 51 in the present modification does not include the distal end pipe sleeve member 54 at the distal end part of the tube main body 52.

(Third Modification)

Figure 14:
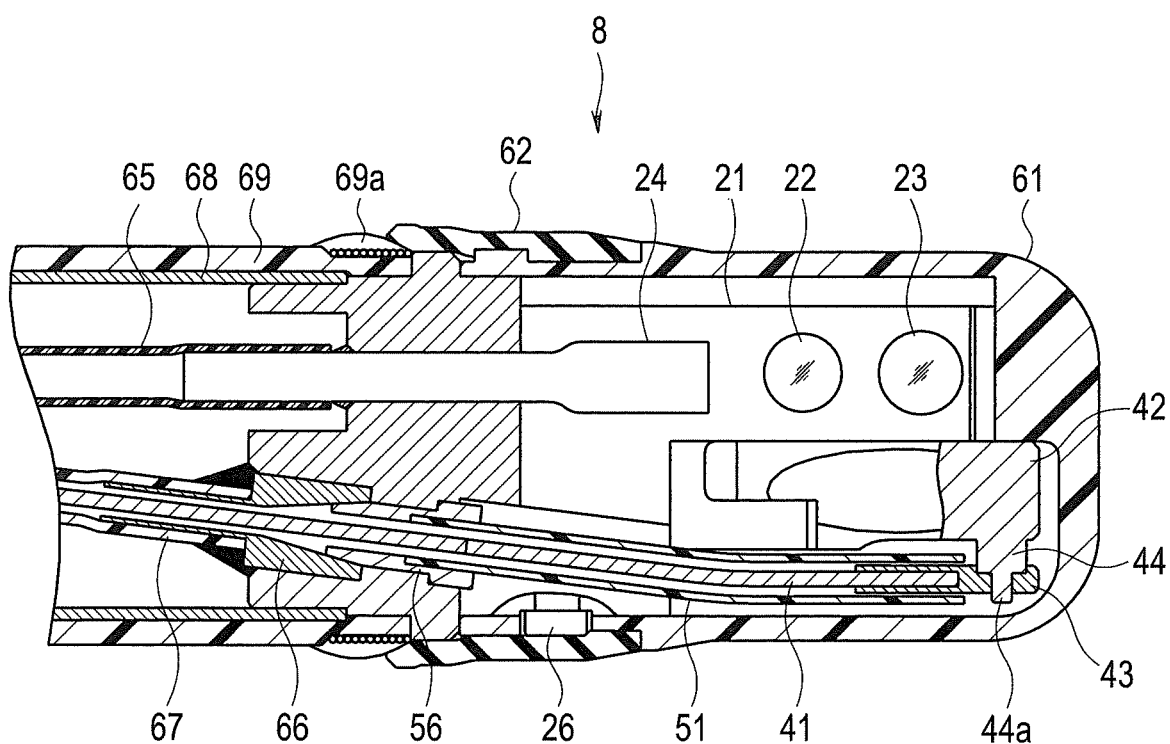
FIG. 14 is a cross-sectional view of a distal end portion of a third modification as viewed from above.
Figure 15:
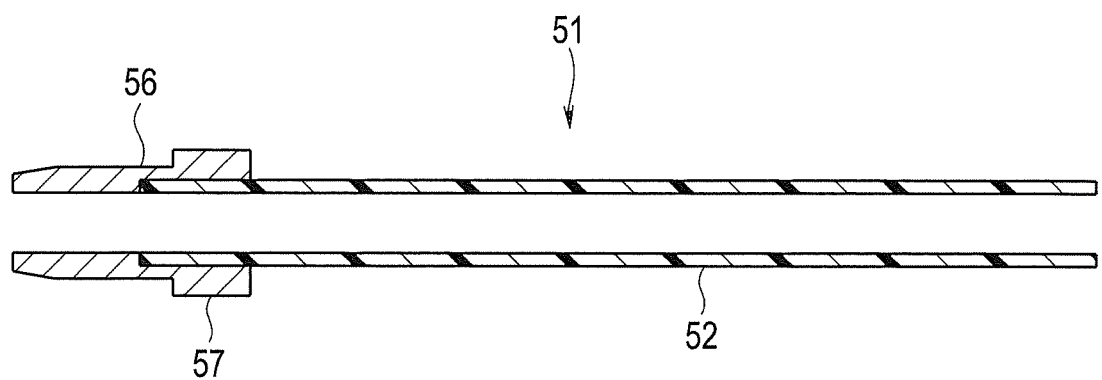
FIG. 15 is a cross-sectional view illustrating a configuration of a flexible tube according to the third modification.

FIG. 14 is a cross-sectional view of a distal end portion of the third modification as viewed from above, and FIG. 15 is a cross-sectional view illustrating a configuration of a flexible tube according to the third modification.

As illustrated in FIGS. 14 and 15, the flexible tube 51 includes, at the proximal end part thereof, a proximal end pipe sleeve 56 made of metal such as stainless steel, or made of rigid resin, similarly as in the second modification. However, the O-ring 58 is not provided to the proximal end pipe sleeve 56.

In addition, the flexible tube 51 includes neither the distal end pipe sleeve member 54 nor the projection portion 53 for retaining water-tightness at the distal end part of the tube main body 52. Such a configuration enables the flexible tube 51 to be manufactured at a low cost. The configuration is effective especially in the case where the flexible tube 51 is a disposable type.

Furthermore, as illustrated in FIG. 14, the wire attaching member 44 and the protrusion 44a may be formed integrally with the raising base 42.

(Fourth Modification)

Figure 16:
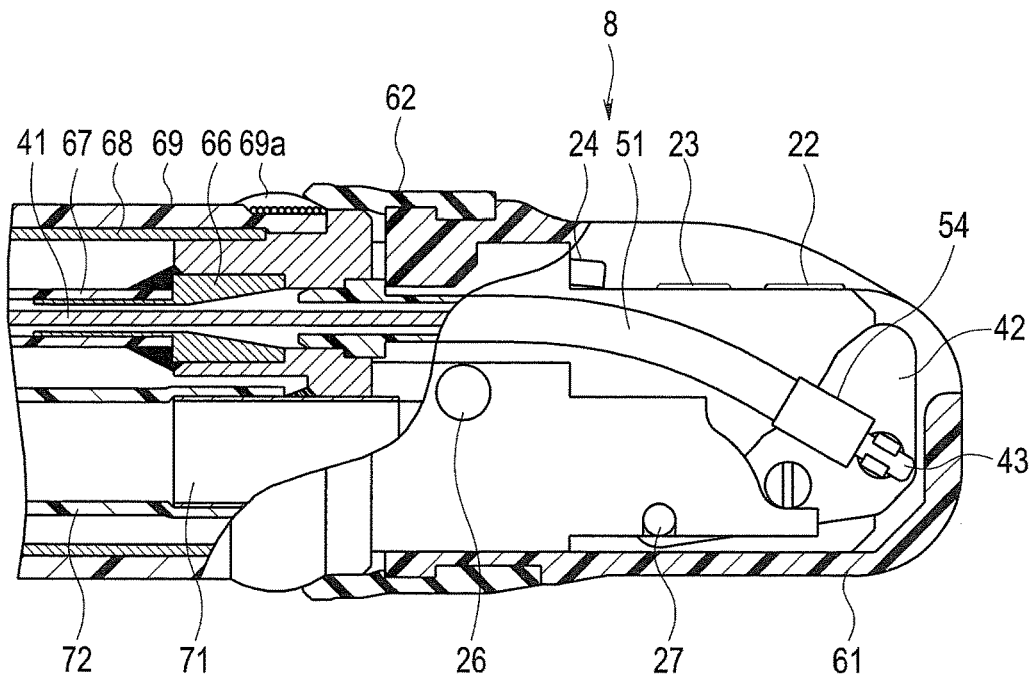
FIG. 16 is a cross-sectional view of a distal end portion of a fourth modification as viewed from a lateral side.
Figure 17:
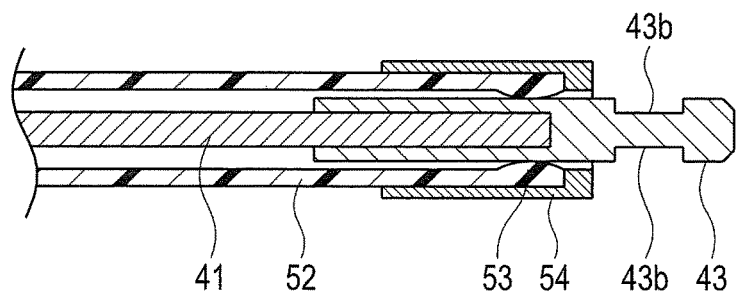
FIG. 17 is a cross-sectional view illustrating a configuration of a distal end part of a raising base operation wire inserted through a flexible tube, according to the fourth modification.
Figure 18:
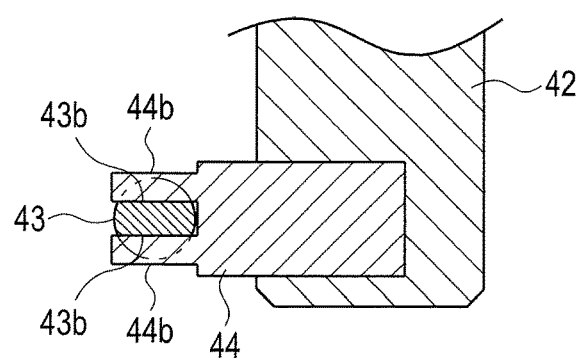
FIG. 18 is a cross-sectional view illustrating a connecting state between a wire and a raising base, according to the fourth modification.

FIG. 16 is a cross-sectional view of a distal end portion of the fourth modification as viewed from the lateral side, FIG. 17 is a cross-sectional view illustrating a configuration of a distal end part of a raising base operation wire inserted through a flexible tube according to the fourth modification, and FIG. 18 is a cross-sectional view illustrating a connecting state between a wire and a raising base, according to the fourth modification.

The connecting configuration between the wire 41 and the raising base 42 may be the one illustrated in FIGS. 16 to 18. That is, the wire terminal member 43 provided at the distal end of the wire 41 may include recessed portions 43b formed in point symmetry, and the wire attaching member 44 of the raising base 42 may include two protrusions 44b for engaging the end portion of the wire attaching member 44 with the two recessed portions 43b of the wire terminal member 43.

(Fifth Modification)

Figure 19:
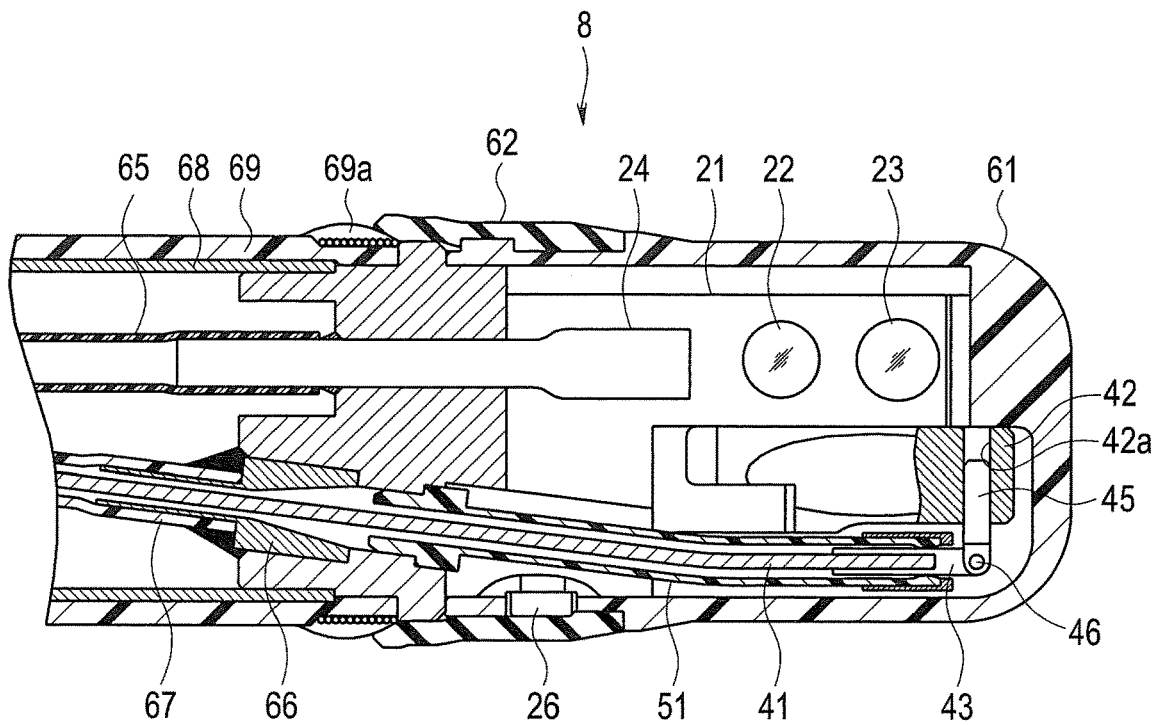
FIG. 19 is a cross-sectional view of a distal end portion of a fifth modification as viewed from above.
Figure 20:
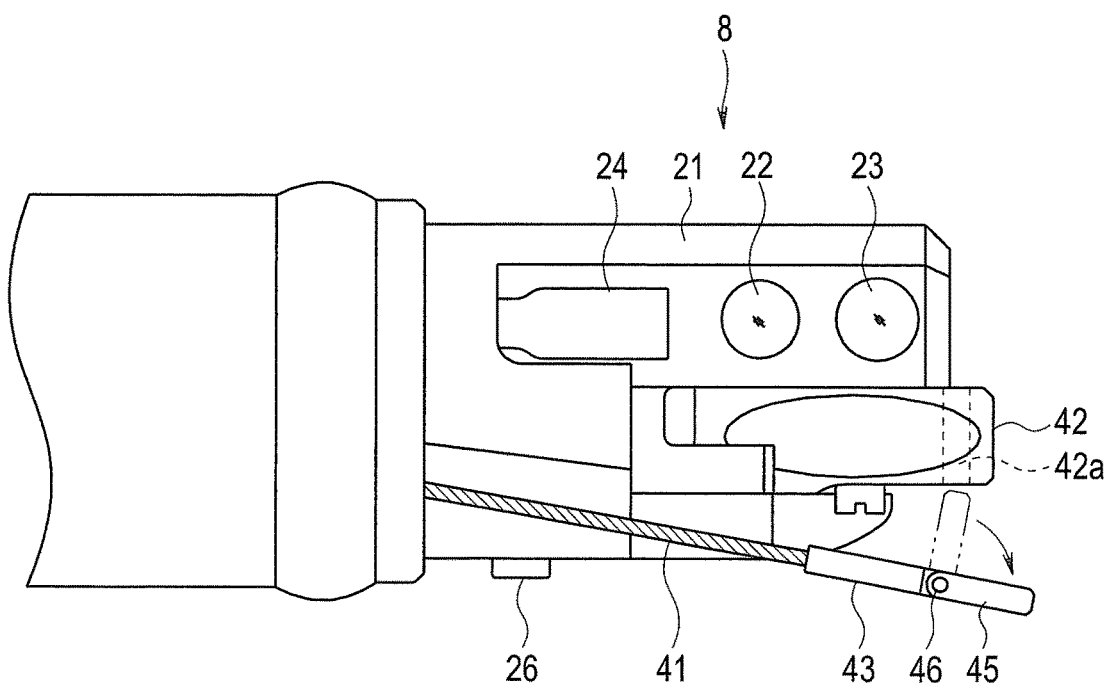
FIG. 20 is a top view of the distal end portion of the fifth modification.

FIG. 19 is a cross-sectional view of a distal end portion of the fifth modification as viewed from above, and FIG. 20 is a top view of the distal end portion of the fifth modification.

The connecting configuration between the wire 41 and the raising base 42 may be the one illustrated in FIGS. 19 and 20. That is, the raising base 42 may include a hole portion 42a that opens on the side surface of the raising base 42, and the wire attaching member 44 may include a bar portion 45 which is configured to be pivotable around a pivot shaft 46 and to be inserted into the hole portion 42a.

Note that when the bar portion 45 is brought into a linear state in accordance with the axis of the wire attaching member 44, the flexible tube 51 can be pulled out from the wire 41.

(Sixth Modification)

Figure 21:
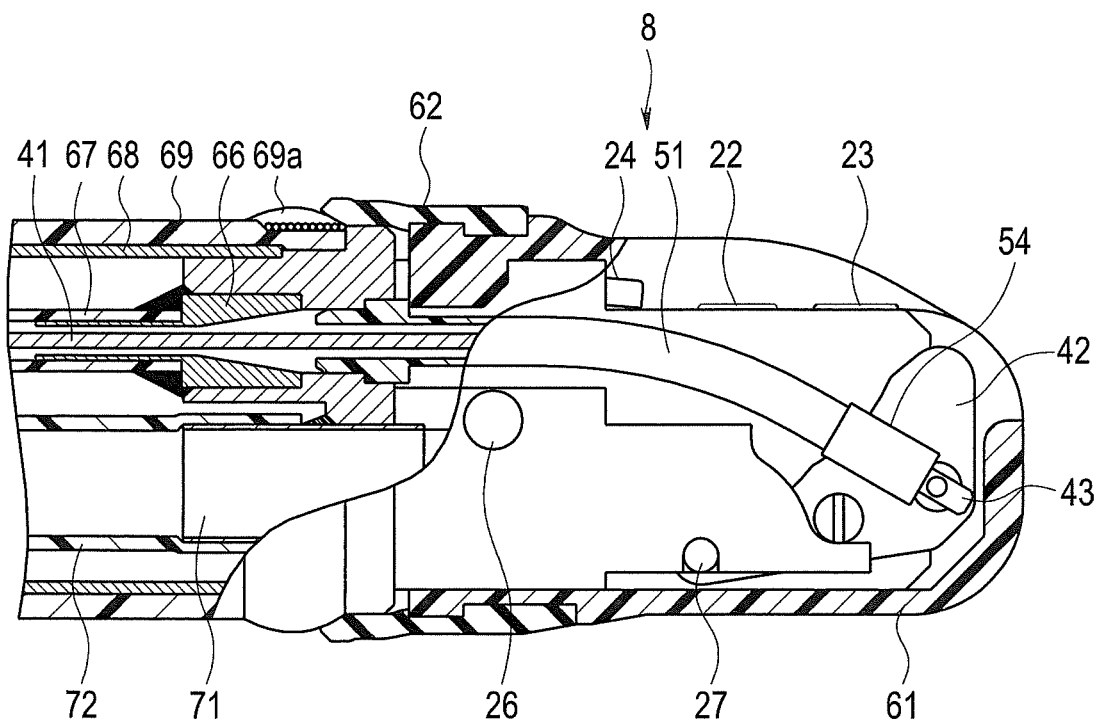
FIG. 21 is a cross-sectional view of a distal end portion of a sixth modification as viewed from the lateral side.
Figure 22:
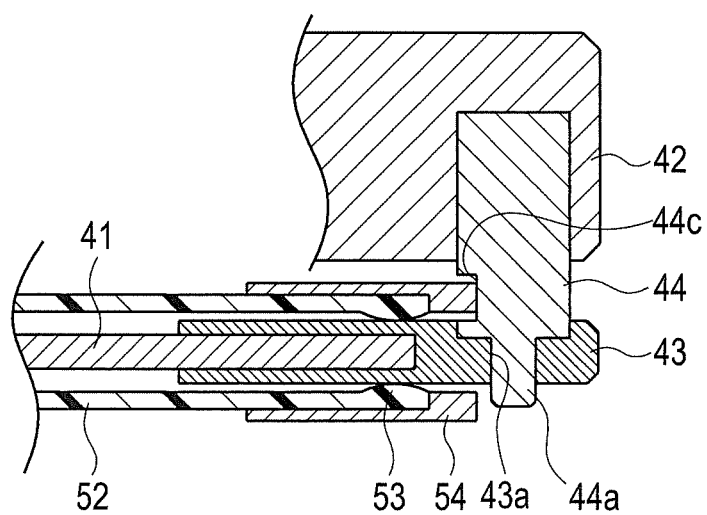
FIG. 22 is a cross-sectional view illustrating a connecting state between a wire and a raising base, according to the sixth modification.
Figure 23:
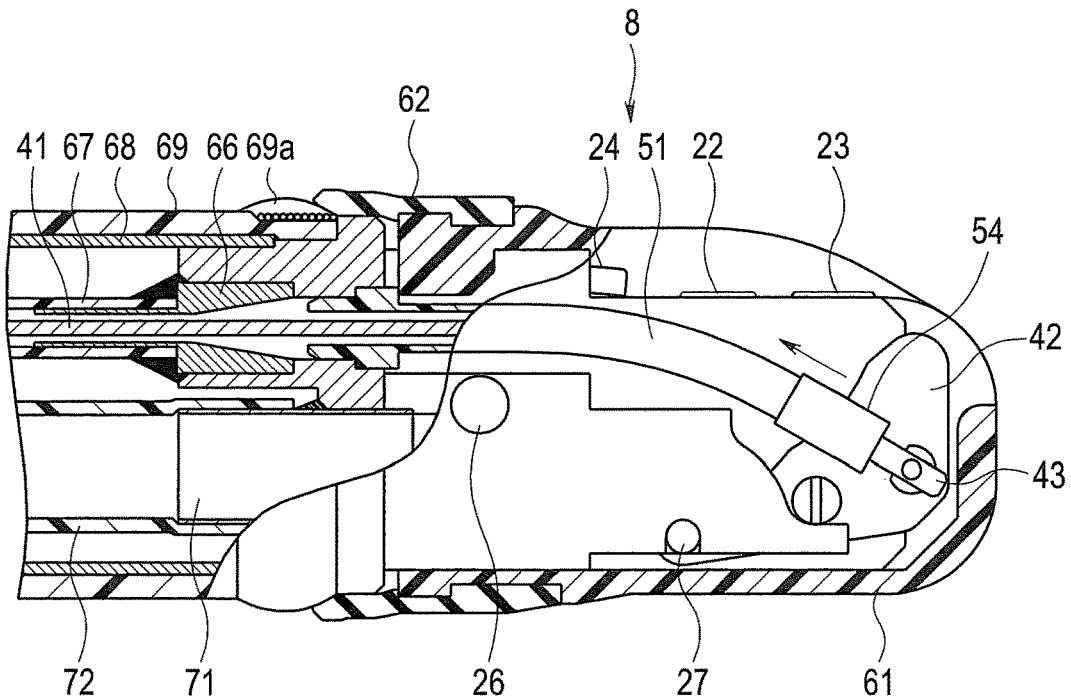
FIG. 23 is a cross-sectional view of the distal end portion of the sixth modification in a state where a flexible tube is compressed, as viewed from a lateral side.
Figure 24:
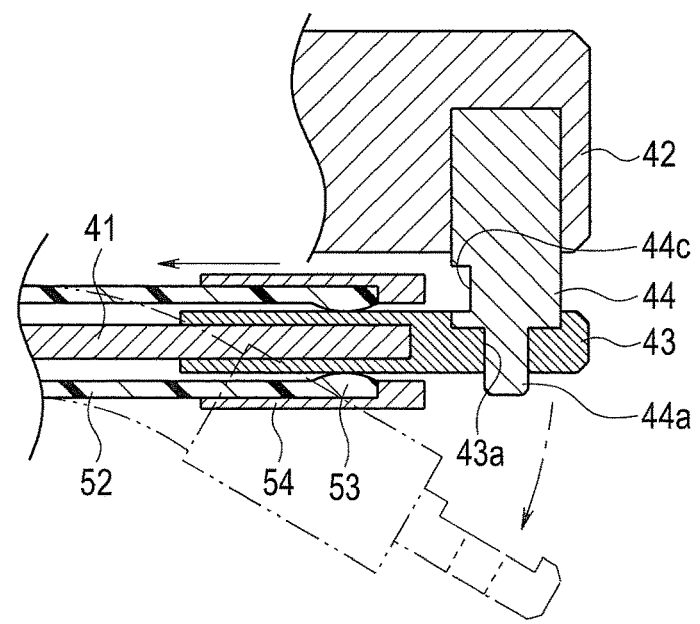
FIG. 24 is a cross-sectional view illustrating a connecting state between the wire and the raising base in a state where the flexible tube is compressed, according to the sixth modification.
Figure 25:
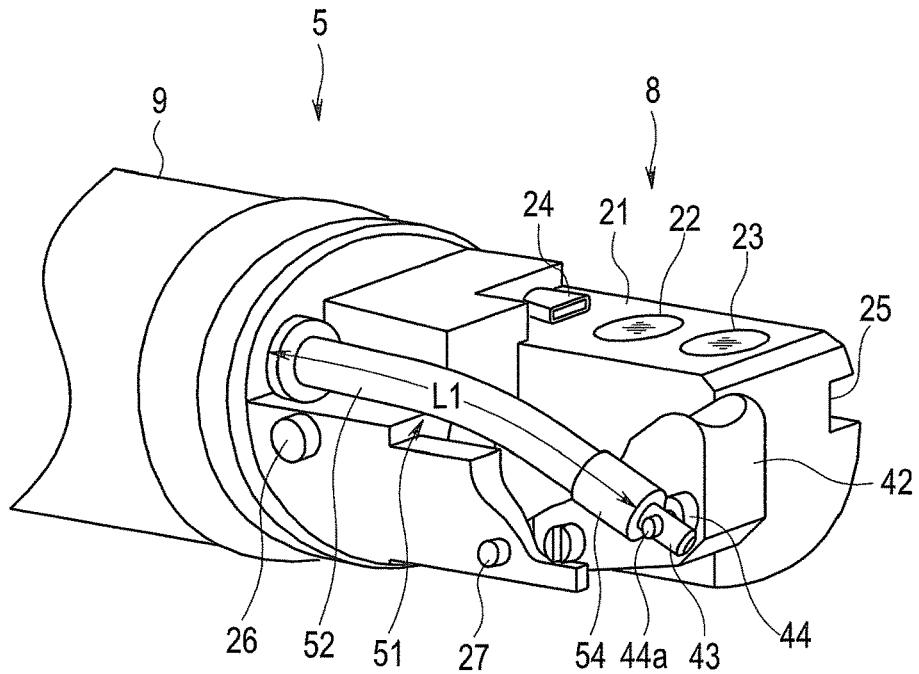
FIG. 25 is a perspective view illustrating a configuration of the distal end portion from which a distal end cover is removed, according to the sixth modification.
Figure 26:
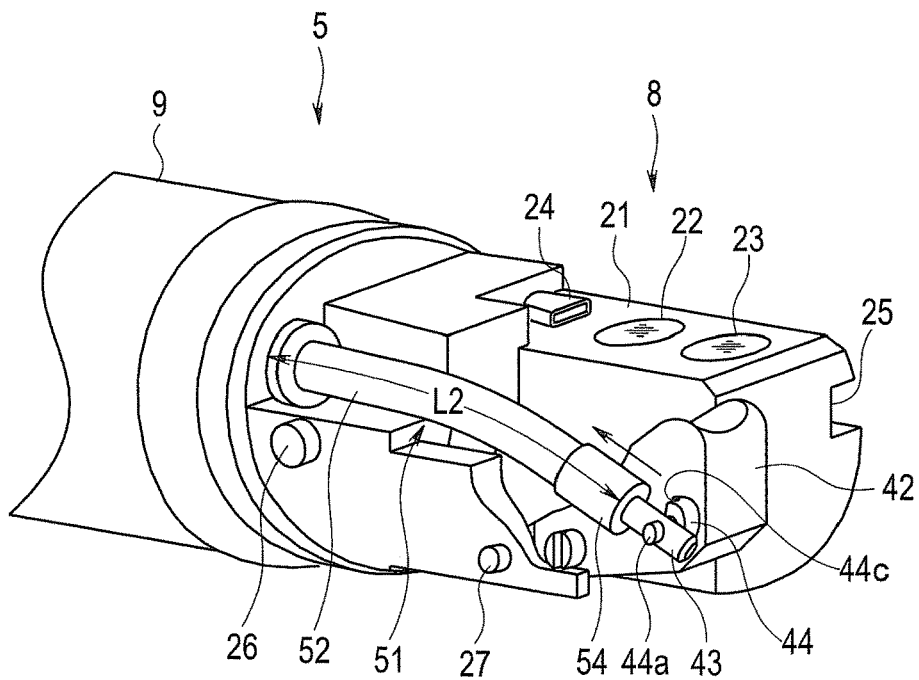
FIG. 26 is a perspective view illustrating the configuration of the distal end portion from which the distal end cover is removed and which is in a state where the flexible tube is compressed, according to the sixth modification.
Figure 27:
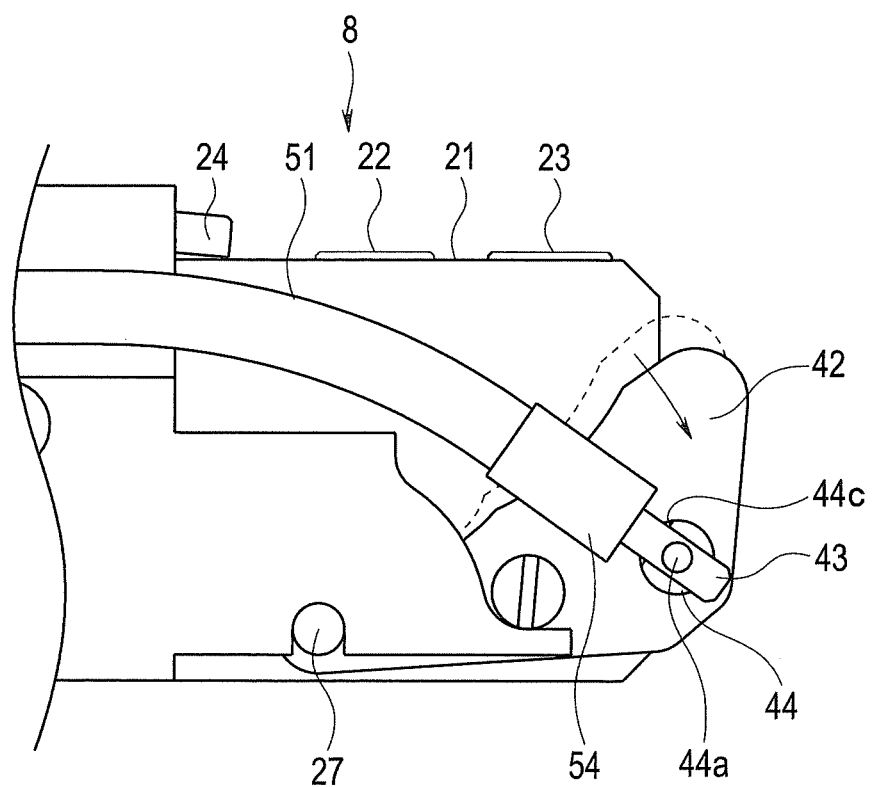
FIG. 27 is a side view of the distal end portion from which the distal end cover is removed, according to the sixth modification.

FIG. 21 is a cross-sectional view of a distal end portion of the sixth modification as viewed from the lateral side, FIG. 22 is a cross-sectional view illustrating a connecting state between a wire and a raising base, according to the sixth modification, FIG. 23 is a cross-sectional view of the distal end portion of the sixth modification in a state where a flexible tube is compressed, as viewed from a lateral side, FIG. 24 is a cross-sectional view illustrating a connecting state between the wire and the raising base in a state where the flexible tube is compressed, according to the sixth modification, FIG. 25 is a perspective view illustrating a configuration of the distal end portion from which a distal end cover is removed, according to the sixth modification, FIG. 26 is a perspective view illustrating the configuration of the distal end portion from which the distal end cover is removed and which is in a state where the flexible tube is compressed, according to the sixth modification, and FIG. 27 is a side view of the distal end portion from which the distal end cover is removed, according to the sixth modification.

As illustrated in FIGS. 21 and 22, the wire attaching member 44 of the raising base 42 may include a recessed locking groove 44c with which the distal end of the distal end pipe sleeve member 54 of the flexible tube 51 is engaged.

Specifically, the locking groove 44c is formed in a recessed shape on the proximal end part of the outer circumference of the wire attaching member 44, and a part of the distal end of the distal end pipe sleeve member 54 having a tubular shape is engaged with the locking groove 44c by a biasing force of the tube main body 52 of the flexible tube 51 to return to the equilibrium length.

In this state, the connection between the wire 41 and the raising base 42 is locked, with the protrusion 44a of the wire attaching member 44 being inserted into the through hole 43a of the wire terminal member 43 provided at the distal end of the wire 41.

In addition, as illustrated in FIGS. 23 and 24, when the flexible tube 51 is compressed along the longitudinal axis direction, the tube main body 52 is contracted, to thereby release the engagement between the locking groove 44c of the wire attaching member 44 and the distal end pipe sleeve member 54. As a result, the wire terminal member 43 can be removed from the wire attaching member 44. Then, the flexible tube 51 can be pulled out from the wire 41.

That is, as illustrated in FIG. 25, the flexible tube 51 is set to have a predetermined equilibrium length L1 at which a part of the distal end of the distal end pipe sleeve member 54 having a tubular shape is engaged with the locking groove 44c by the biasing force of the tube main body 52. As illustrated in FIG. 26, when the flexible tube 51 is compressed in the proximal end direction to contract the tube main body 52 to a length L2, the engagement between the locking groove 44c of the wire attaching member 44 and the distal end pipe sleeve member 54 is released. In this state, the wire terminal member 43 can be removed from the wire attaching member 44.

With such a configuration, even if the distal end cover 61 is removed from the distal-end constituting portion 21, the connecting state between the wire 41 and the raising base 42 is maintained, to thereby prevent the wire 41 from coming off naturally from the raising base 42.

Note that, in the state where the distal end cover 61 is attached to the distal-end constituting portion 21 as illustrated in FIG. 21, by removing the distal end cover 61 from the distal-end constituting portion 21, the raising base 42 may be allowed to further pivot from the tilted position as illustrated in FIG. 27 (in the clockwise direction viewed toward the paper surface of the figure), and thereby the raising base 42 may be tilted to the maximum.

That is, the raising base 42 is set so as to be slightly raised by contacting the distal end cover 61 when the distal end cover 61 is attached to the distal-end constituting portion 21. In addition, the flexible tube 51 is set to have the predetermined equilibrium length L1 at which a part of the distal end of the distal end pipe sleeve member 54 is engaged with the locking groove 44c.

With such a configuration, when the distal end cover 61 is removed from the distal-end constituting portion 21 and the raising base 42 is tilted to the maximum, the distal end pipe sleeve member 54 comes off naturally from the locking groove 44c of the wire attaching member 44. As a result, the wire terminal member 43 can be removed from the wire attaching member 44.

Such a configuration eliminates a need for the operation of compressing the flexible tube 51 to contract the tube main body 52 when the wire 41 is detached from the raising base 42.

(Seventh Modification)

Figure 28:
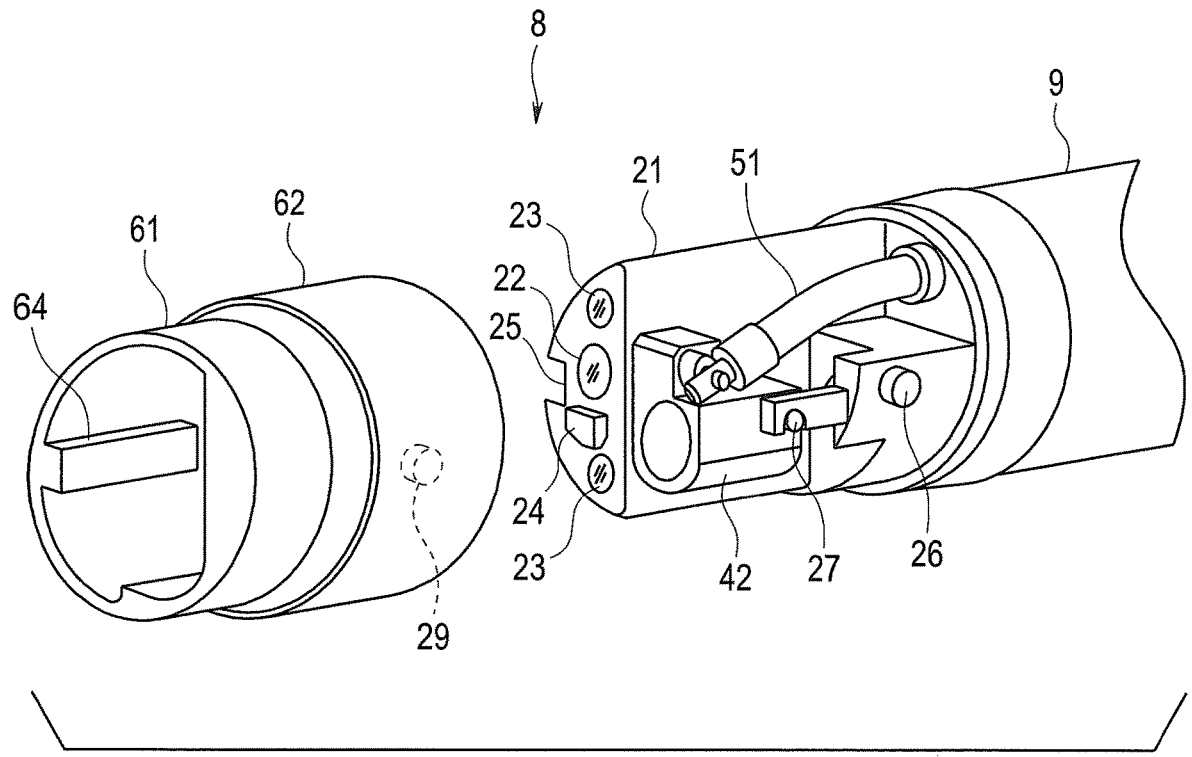
FIG. 28 is an exploded perspective view illustrating a distal end portion of an endoscope, a visual field direction of which is a front-viewing direction, according to a seventh modification.
Figure 29:
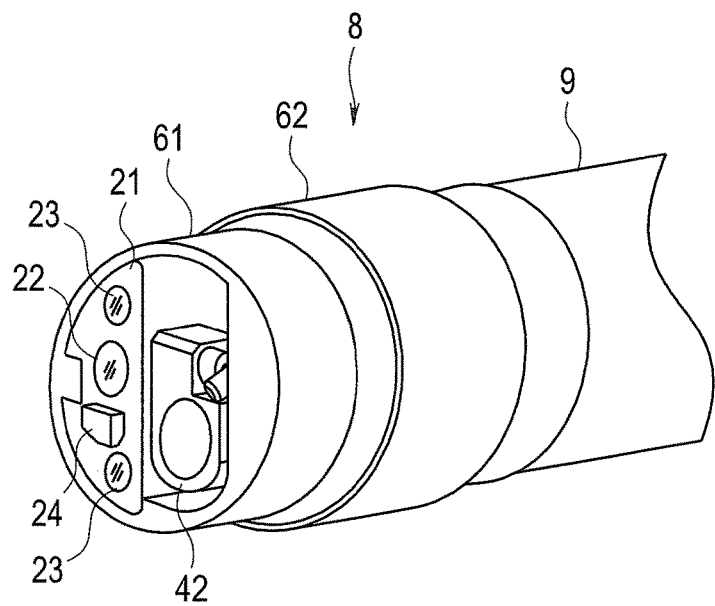
FIG. 29 is a perspective view illustrating the distal end portion of the endoscope, the visual field direction of which is the front-viewing direction, according to the seventh modification.

FIG. 28 is an exploded perspective view illustrating a distal end portion of an endoscope, a visual field direction of which is a front-viewing direction, according to a seventh modification, and FIG. 29 is a perspective view illustrating the distal end portion of the endoscope, the visual field direction of which is the front-viewing direction, according to the seventh modification.

In the technique described above, the configuration of the endoscope 1 in which the field of view direction is side-viewing direction or oblique-viewing direction has been described as an example. However, the present invention is not limited to the example, but may be applicable to an endoscope having a configuration in which the field of view direction is a front-viewing direction, the distal end cover 61 is configured to be mounted to and removed from the distal-end constituting portion 21, and the raising base 42 as a movable portion is provided in the distal end portion 8, as illustrated in FIGS. 28 and 29.

Reference Example

Figure 30:
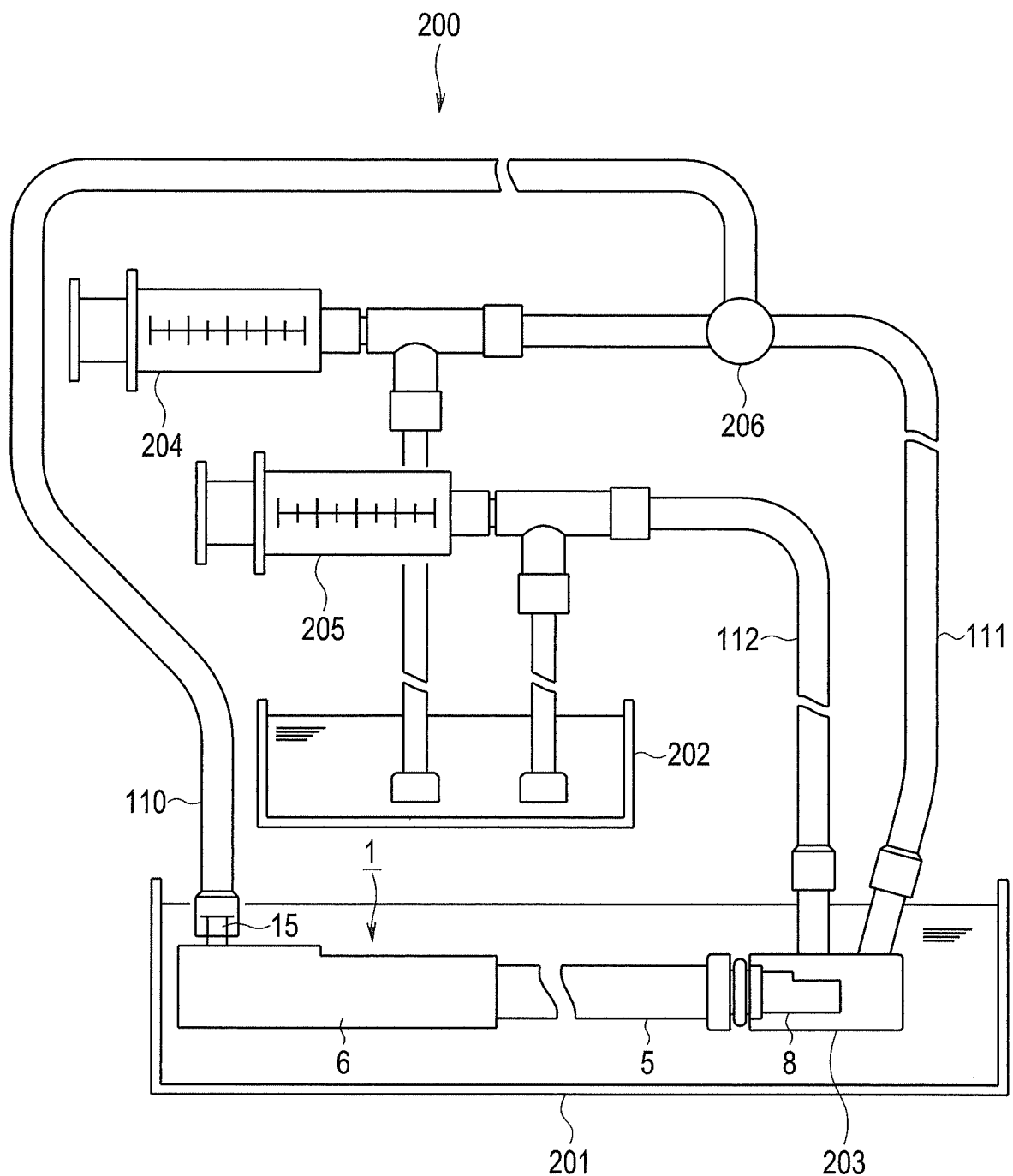
FIG. 30 is a plan view illustrating a cleaning device for endoscope according to a reference example.

FIG. 30 is a plan view illustrating a cleaning device for an endoscope according to a reference example.

Hereinafter, description will be made on an example of a cleaning device 200 for cleaning and disinfecting the endoscope 1 as illustrated in FIG. 30.

The cleaning device 200 includes a cleaning tank 201 in which the endoscope 1 is housed, and a liquid storage tank 202 in which a liquid such as a cleaning solution, a disinfectant solution, or the like is stored.

In addition, the cleaning device 200 includes a cleaning tube 110 to be connected to the cleaning tube connector 15 of the endoscope 1, a cleaning device main body 203 configured to be mounted to the distal end portion 8 from which the distal end cover 61 and the flexible tube 51 are removed, and a first liquid feeding tube 111 and a second liquid feeding tube 112, each have one end portion connected to the cleaning device main body 203.

In addition, the cleaning tube 110 is connected to a three-way stopcock 206 provided at the halfway of the first liquid feeding tube 111.

The first liquid feeding tube 111 is configured such that a first syringe 204 is connected to the halfway part thereof located on the liquid storage tank 202 side with respect to the three-way stopcock 206. The other end portion of the first liquid feeding tube 111 is put in the liquid storage tank 202. The second liquid feeding tube 112 is configured such that a second syringe 205 is connected to the halfway part thereof, and the other end portion of the second liquid feeding tube 112 is put in the liquid storage tank 202.

The cleaning device 200 configured as described above is capable of cleaning and disinfecting the endoscope 1 by supplying the liquids such as a cleaning solution and a disinfectant solution stored in the liquid storage tank 202 to the endoscope 1 by the first syringe 204 and the second syringe 205.

Note that the user switches the conduits of the three-way stopcock 206, to thereby switch the liquid feeding path by the first syringe 204 between the cleaning tube 110 and the first liquid feeding tube 111, and performs cleaning and disinfecting on the wire covering tube 67 in the endoscope 1 and the part around the raising base 42 in the distal end portion 8 housed in the cleaning device main body 203.

At this time, in the cleaning device 200, the liquid such as the cleaning solution, the disinfectant solution, or the like is fed to one of the cleaning tube 110 and the first liquid feeding tube 111 by the three-way stopcock 206. Such a configuration enables a large amount of liquid to be fed with a great force to the wire covering tube 67 or the part around the raising base 42 in the distal end portion 8, which enables the cleaning and disinfecting of the endoscope 1 to be easily performed.

Note that, in the above-described endoscope 1, the configuration including the raising base 42 for raising and lowering the treatment instrument has been described as an example. However, the present invention is not limited to the example, but the endoscope 1 may have a configuration in which a swinging base, as a movable portion, for swinging the treatment instrument and the like is provided instead of the raising base 42.

The configurations recited in the above-described embodiment and the modifications may be combined with each other, and various modifications are possible at the practical stage in a range without departing from the gist of the invention. Furthermore, each of the above embodiments includes the inventions at various stages, and various inventions can be extracted by appropriately combining a plurality of disclosed constituent elements.

For example, even if some of the components are removed from all the components shown in the above embodiment and modifications, a configuration from which the components are eliminated can be extracted as an invention insofar as the recited problem can be solved and the recited effects of the invention can be obtained.

The present invention is capable of providing an endoscope which enables easy replacement/repair and cleaning/disinfecting of the tube covering the wire configured to drive the movable portion provided in the distal end portion of the insertion portion, and which reduces a burden of the medical workers at the time of cleaning and disinfecting the endoscope.

What is claimed is:

1. An endoscope comprising:
    a distal-end body provided at a distal end portion of an insertion portion;
    a distal end cover configured for attachment to and detachment from the distal-end body;
    a movable body provided in the distal-end body to move relative to the distal-end body;
    a wire configured to move the movable body by being pulled or relaxed;
    a connecting assembly configured to releasably connect the wire to the movable body, the connecting assembly being configured to only detach the wire from the movable body when the distal end cover is removed from the distal-end body; and
    a tube having flexibility through which the wire is inserted, the tube being disposed in the distal end portion and is detachably attached to the distal-end body;
    wherein the connecting assembly comprises:
        a protrusion protruding from one of the movable body or the wire, the protrusion protruding in a direction intersecting a longitudinal direction of the wire, and
        an other of the movable body and the wire having a portion configured to release from the protrusion in the direction when the distal end cover is removed from the distal-end body.

2. The endoscope according to claim 1, wherein a proximal end of the tube is water-tightly connected to the distal-end body, and the tube comprises a projection formed in a circumferential direction on an inner circumference of a distal end of the tube, the projection being brought into close contact with the wire to retain water-tightness.

3. The endo scope according to claim 1, wherein the tube comprises, at a proximal end part of the tube, a seal configured to retain water-tightness of a connecting part between the tube and the distal-end body.

4. The endoscope according to claim 1, wherein the tube comprises an outward flange formed at a proximal end part of the tube, and the outward flange is configured to come into contact with a proximal end surface of the distal end cover mounted on the distal-end body by the proximal end surface pressing the outward flange against the distal-end body.

5. The endoscope according to claim 1, wherein the protrusion protrudes from the movable body.

6. The endoscope according to claim 5, wherein the protrusion is integrally formed with the movable body.

7. The endoscope according to claim 5, wherein
the protrusion comprising first and second prongs extending from the movable body and opposing each other; and
the portion comprises opposing surfaces provided at a distal end of the wire the opposing surfaces being configured to releasably retain the first and second prongs.

8. The endoscope according to claim 5, wherein
the protrusion comprises a concavity; and
the endoscope further comprises a sleeve disposed on a distal end of the tube, the sleeve having a projection for matingly engaging the concavity;
wherein the tube is axially compressible to release the projection from the concavity when the distal end cover is removed from the distal-end body.

9. The endoscope according to claim 1, wherein the movable body is one of a raising base or swinging base provided pivotally in the distal-end body, and the one of the raising base or the swinging base is configured to change an instrument direction of a treatment instrument led out from the distal end portion.

10. The endoscope according to claim 1, wherein the tube being configured to only be detachable from the distal-end body when the distal end cover is removed from the distal-end body and the wire is detached from the movable body.

11. The endoscope according to claim 1, wherein
the protrusion is rotatably connected to a distal end of the wire; and
the portion is a hole formed in the movable body, the hole being formed to extend in the direction.

12. An endoscope comprising:
a distal-end body provided at a distal end portion of an insertion portion, the distal end body being configured to accept a removable distal end cover;
a movable body provided in the distal-end body to move relative to the distal-end body;
a wire configured to move the movable body by being pulled or relaxed;
a connecting assembly configured to releasably connect the wire to the movable body, the connecting assembly being configured to only detach the wire from the movable body when the distal end cover is removed from the distal-end body; and
a tube having flexibility through which the wire is inserted, the tube being disposed in the distal end portion and is detachably attached to the distal-end body;
wherein the connecting assembly comprises:
a protrusion protruding from one of the movable body or the wire, the protrusion protruding in a direction intersecting a longitudinal direction of the wire, and
an other of the movable body and the wire having a portion configured to release from the protrusion in the direction when the distal end cover is removed from the distal-end body.

13. The endoscope according to claim 12, wherein the tube being configured to only be detachable from the distal-end body when the distal end cover is removed from the distal-end body and the wire is detached from the movable body.

14. The endoscope according to claim 12, wherein a proximal end of the tube is water-tightly connected to the distal-end body, and the tube comprises a projection formed in a circumferential direction on an inner circumference of a distal end of the tube, the projection being brought into close contact with the wire to retain water-tightness.

15. The endoscope according to claim 12, wherein the tube comprises an outward flange formed at a proximal end part of the tube, and the outward flange is configured to come into contact with a proximal end surface of the distal end cover mounted on the distal-end body by the proximal end surface pressing the outward flange against the distal-end body.

16. The endoscope according to claim 12, wherein the protrusion protrudes from the movable body.

17. The endoscope according to claim 16, wherein the protrusion is integrally formed with the movable body.

18. The endoscope according to claim 12, wherein the movable body is one of a raising base or swinging base provided pivotally in the distal-end body, and the one of the raising base or the swinging base is configured to change an instrument direction of a treatment instrument led out from the distal end portion.

19. An insertion section comprising:
a distal-end body being configured to accept a removable distal end cover;
a movable body provided in the distal-end body to move relative to the distal-end body;
a wire configured to move the movable body by being pulled or relaxed;
a connecting assembly configured to releasably connect the wire to the movable body, the connecting assembly being configured to only detach the wire from the movable body when the distal end cover is removed from the distal-end body; and
a tube having flexibility through which the wire is inserted, the tube being disposed in the distal end portion and is detachably attached to the distal-end body;
wherein the connecting assembly comprises:
a protrusion protruding from one of the movable body or the wire, the protrusion protruding in a direction intersecting a longitudinal direction of the wire, and
an other of the movable body and the wire having a portion configured to release from the protrusion in the direction when the distal end cover is removed from the distal-end body.

20. The insertion section according to claim 19, wherein the tube being configured to only be detachable from the distal-end body when the distal end cover is removed from the distal-end body and the wire is detached from the movable body.

* * * * *